United States Patent
Davuluri et al.

(10) Patent No.: US 10,113,201 B2
(45) Date of Patent: Oct. 30, 2018

(54) METHODS AND COMPOSITIONS FOR DIAGNOSIS OF GLIOBLASTOMA OR A SUBTYPE THEREOF

(71) Applicants: The Wistar Institute of Anatomy and Biology, Philadelphia, PA (US); The Trustees of the University of Pennsylvania, Philadelphia, PA (US)

(72) Inventors: Ramana V. Davuluri, Haverford, PA (US); Sharmistha Pal, Downingtown, PA (US); Yingtao Bi, Philadelphia, PA (US); Louise C. Showe, Media, PA (US); Donald M. O'Rourke, Wynnewood, PA (US); Luke Macyszyn, Philadelphia, PA (US)

(73) Assignees: The Wistar Institute of Anatomy and Biology, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/782,116

(22) PCT Filed: Apr. 4, 2014

(86) PCT No.: PCT/US2014/032966
§ 371 (c)(1),
(2) Date: Oct. 2, 2015

(87) PCT Pub. No.: WO2014/165753
PCT Pub. Date: Oct. 9, 2014

(65) Prior Publication Data
US 2016/0060704 A1 Mar. 3, 2016

Related U.S. Application Data

(60) Provisional application No. 61/808,878, filed on Apr. 5, 2013, provisional application No. 61/937,215, filed on Feb. 7, 2014.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 6,248,526 B1 * 6/2001 Weimer ............... C12Q 1/6846
435/183
2001/0053519 A1 * 12/2001 Fodor ................. B01J 19/0046
435/6.11

2010/0167939 A1 7/2010 Aldape et al.
2011/0105340 A1 5/2011 Tian et al.
2012/0003209 A1 * 1/2012 Tran ..................... C12N 15/113
424/133.1

OTHER PUBLICATIONS

Korshunov (Acta Neuopathol 2006 vol. 111 p. 465).*
NEB catalog (1998/1999 pp. 121, 284).*
Rhee (Applied and Environmental Microbiology Jul. 2004 p. 4303).*
Zhang, Z. et al., Isoform level expression profiles provide better cancer signatures than gene level expression profiles, Genome Medicine, Apr. 2013, 5(33): 1-13.
Zhang, Z. et al., Unique Genome-Wide Map of TCF4 and STAT3 Targets Using ChIP-seq reveals their association with new molecular subtypes of glioblastoma, Neuro-Oncology, Jan. 2013, 15(3): 279-289.
Zhang, Z. et al., HOTAIR, a cell cycle-associated long noncoding RNA and a strong predictor of survival, is preferentially expressed in classical and mesenchymal glioma, Neuro-Oncology, Nov. 2013, 15(12): 1595-1603.
GenBank Direct Submission AF490843, *Homo sapiens* clone PAC 70L19, HOXC gene cluster. Mar. 2003.
Magalhaes, A.X., The transcriptome of the Oncogenic HOXA9 homeoprotein in human glioblastoma: functional and clinical relevance, Jan. 2013 (Abstract).
International Search Report dated Sep. 10, 2014 in corresponding International Patent Application No. PCT/US2014/32966 filed Apr. 4, 2014.
Written Opinion dated Sep. 10, 2014 in corresponding International Patent Application No. PCT/US2014/32966 filed Apr. 4, 2014.
Dunn, G.P. et al., Emerging insights into the molecular and cellular basis of glioblastoma, Genes & Development, Apr. 2012, 26(8): 756-784.
Vitucci, M. et al., Gene expression profiling of gliomas: merging genomic and histopathological classification for personalised therapy, British Journal of Cancer, Nov. 2010, 104: 545-553.
Verhaak, R.G. et al., An integrated genomic analysis identifies clinically relevant subtypes of glioblastoma characterized by abnormalities in PDGFRA, IDH1, EGFR and NF1, Cancer Cell, Jan. 2010, 17(1): 98-110.
Li, A. et al., Unsupervised Analysis of Transcriptomic Profiles Reveals Six Glioma Subtypes, Cancer Research, Mar. 2009, 69(5): 2091-2099.

(Continued)

*Primary Examiner* — Katherine D Salmon
(74) *Attorney, Agent, or Firm* — Howson & Howson LLP

(57) ABSTRACT

An isoform-level gene panel is disclosed that can accurately classify a glioblastoma subtype from a tumor sample. Such an isoform level gene panel comprises the 121 to 214 target isoforms identified in Table 1. Also disclosed are reagents for quantitatively detecting the expression or activity of the target isoforms of Table 1 in a patient sample. For example, such ligands can be PCR primer and probes sets. This isoform-level gene panel and reagents for detection of the isoforms are useful in an isoform-level assay for diagnosis of the molecular subtype of a glioblastoma in a patient. The assay employs algorithms and a novel computer program that performs the functions of FIG. 8. In one aspect, the assay is a high-throughput format.

7 Claims, 17 Drawing Sheets
Specification includes a Sequence Listing.

(56) References Cited

OTHER PUBLICATIONS

Olson, S. and Berger, A.C., Genome-Based Diagnostics: Clarifying Pathways to Clinical Use: Workshop Summary, Mar. 2012.
Bemmo, A. et al., Exon-Level Transcriptome Profiling in Murine Breast Cancer Reveals Splicing Changes Specific to Tumors with Different Metastatic Abilities, PLoS One, Aug. 2010, 5(8): e11981.
Boidot, R. et al., Predictive value of survivin alternative transcript expression in locally advanced breast cancer patients treated with neoadjuvant chemotherapy, International Journal of Molecular Medicine, Dec. 2008, 23: 285-291.
Lapuk, A. et al., Exon-level microarray analyses identify alternative splicing programs in breast cancer, Molecular Cancer Research, Jul. 2010, 8(7): 961-974.
Misquitta-Ali, C.M. et al., Global Profiling and Molecular Characterization of Alternative Splicing Events Misregulated in Lung Cancer, Molecular and Cellular Biology, Jan. 2011, 31(1): 138-150.
Wang, L. et al., SF3B1 and Other Novel Cancer Genes in Chronic Lymphocytic Leukemia, The New England Journal of Medicine, Dec. 2011, 365(26): 2497-2506.
Friboulet, L. et al., ERCC1 Isoform Expression and Repair in Non-Small-Cell Lung Cancer, The New England Journal of Medicine, Mar. 2013, 368(12): 1101-1110.
Turro, E. et al., MMBGX: a method for estimating expression at the isoform level and detecting differential splicing using whole-transcript Affymetrix arrays, Nucleic Acids Research, Oct. 2009, 38(1): e4.
Workman, C. et al., A new non-linear normalization method for reducing variability in DNA microarray experiments, Genome Biology, Aug. 2002, 3(9): research0048.1-0048.16.
Gaujoux, R and Seoighe, C., A Flexible R Package for Nonnegative Matrix Factorization, BMC Bioinformatics, Jul. 2010, 11: 367.
Diaz-Uriarte, R. and Alvarez De Andres, Gene selection and classification of microarray data using random forest, BMC Bioinformatics, Jan. 2006, 7(3): 1-13 doi:10.1186/1471-2105-7-3.
Breiman, L, Random Forests, Machine Learning, Oct. 2001, 45(1): 5-32.
Rousseeuw, P.J., Silhouettes: a graphical aid to the interpretation and validation of cluster analysis, Journal of Computational and Applied Mathematics, Nov. 1986, 20: 53-65.
Liu, H. et al., Discretization: An Enabling Technique, Data Mining and Knowledge Discovery, Oct. 2002, 6(4): 393-423.
Brennan, C. et al., Glioblastoma Subclasses Can Be Defined by Activity among Signal Transduction Pathways and Associated Genomic Alterations, PLoS One, Nov. 2009, 4(11): e7752.
Lu, K.V. et al., VEGF inhibits tumor cell invasion and mesenchymal transition through a MET/VEGFR2 complex, Cancer Cell, Jul. 2012, 22(1): 21-35.
Lee, Y. et al., Gene expression analysis of glioblastomas identifies the major molecular basis for the prognostic benefit of younger age, BMC Medical Genomics, Oct. 2008, 1:52.
Feero, W.G. et al., Genomic Medicine—An Updated Primer, The New England Journal of Medicine, May 2010, 362(21): 2001-2011.
McDermott, U. et al., Genomics and the Continuum of Cancer Care, The New England Journal of Medicine, Jan. 2011, 364(4): 340-350.
Pal, S. et al., Alternative transcription exceeds alternative splicing in generating the transcriptome diversity of cerebellar development, Genome Research, May 2011, 21: 1260-1272.
Phillips, H.S. et al., Molecular subclasses of high-grade glioma predict prognosis, delineate a pattern of disease progression, and resemble stages in neurogenesis, Cancer Cell, Mar. 2006, 9: 157-173.
Shen, R. et al., Integrative Subtype Discovery in Glioblastoma Using iCluster, PLoS One, Apr. 2012, 7(4): e35236.
Sturm, D. et al., Hotspot Mutations in H3F3A and IDH1 Define Distinct Epigenetic and Biological Subgroups of Glioblastoma, Cancer Cell, Oct. 2012, 22: 425-437.
Liang, Y. et al., Gene expression profiling reveals molecularly and clinically distinct subtypes of glioblastoma multiforme, PNAS, Apr. 2005, 102(16): 5814-5819.
Shirahata, M. et al., Gene Expression-BasedMolecular Diagnostic SystemforMalignant Gliomas Is Superior to Histological Diagnosis, Dec. 2007, 13(14): 7341-7356.
Yan, H. et al., IDH1 and IDH2 Mutations in Gliomas, The New England Journal of Medicine, Feb. 2009, 360(8): 765-773.
Hayden, E.C., Life is Complicated, Nature, Apr. 2010, 464: 664-667.
Warnat, P. et al., Cross-platform analysis of cancer microarray data improves gene expression based classification of phenotypes, BMC Bioinformatics, Nov. 2005, 6: 265.
Manilich, E. et al., Classification of large microarray datasets using fast random forest construction, Journal of Bioinformatics and Computational Biology, Apr. 2011, 9: 251-267.
Pal, S. et al., Isoform-level gene signature improves prognostic stratification and accurately classifies glioblastoma subtypes, Nucleic Acids, Jan. 2014, 42(3): 1-11.
International Preliminary Report on Patentability dated Oct. 15, 2015 in corresponding International Application No. PCT/US14/32966 filed on Apr. 4, 2014.
Ward, D. C. and Reich, E., Fluorescence Studies of Nucleotides and Polynucleotides, The Journal of Biological Chemistry, Mar. 1969, 244(5):1228-1237.
Walsh, J. M. and Beuning, P. J., Synthetic Nucleotides as Probes of DNA Polymerase Specificity, Journal of Nucleic, Jan. 2012, 2012(Article ID 530963):1-17.
Robins, R. K. et al., Structure of the nucleoside Antibioitics Formycin, Formycin B and Laurosin (1), J. Heterocyclic Chem, Mar. 1966, 3:110-114.

\* cited by examiner

Figure 1A
Figure 1B
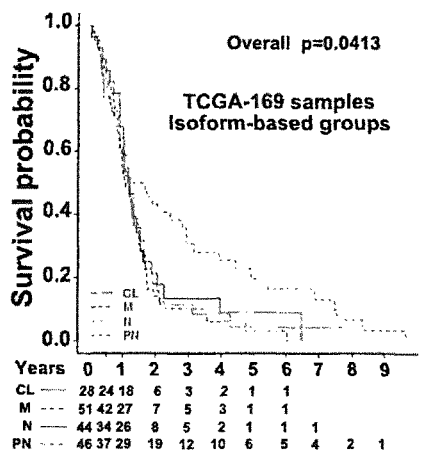
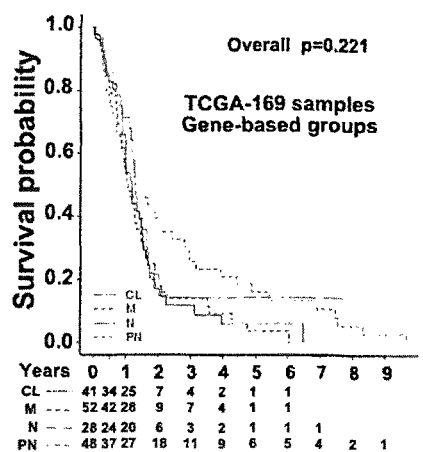
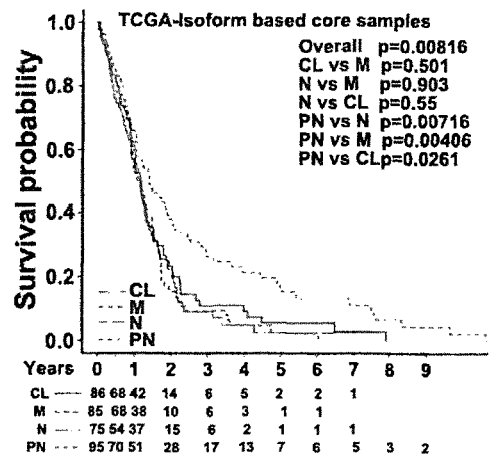
Figure 2

Figure 3A
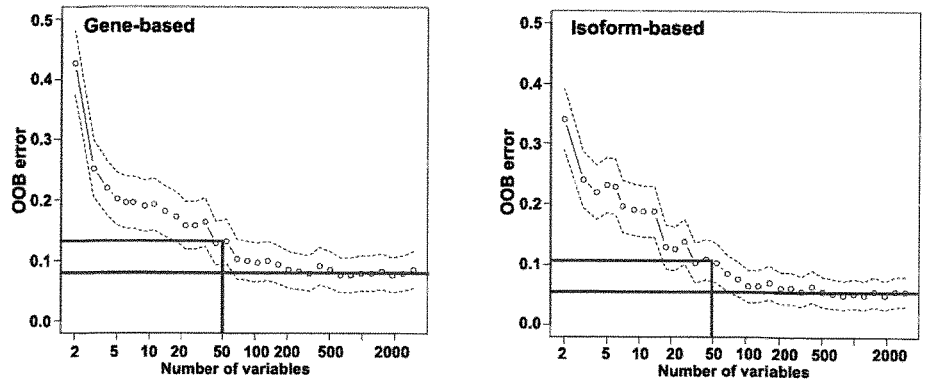
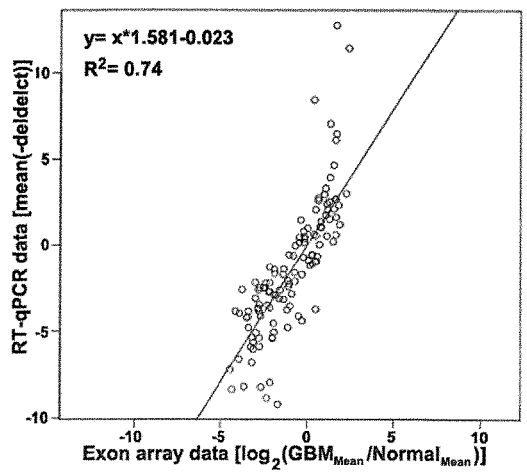
Figure 3B
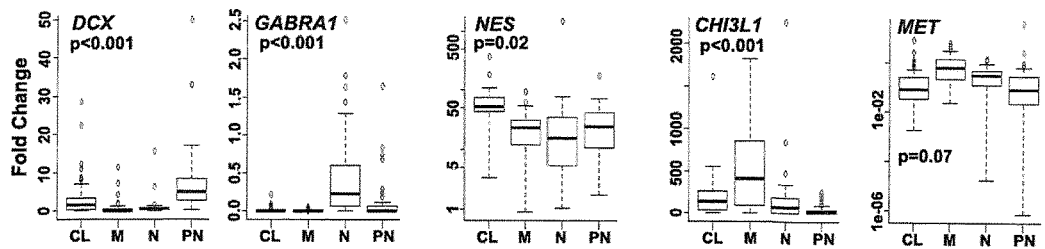
Figure 3C

```
######### ##########################discretization(FCCV values)
and feature selection
############## dividing the whole data set into training and
testing t1<-sample(rownames(nmfclu2)[nmfclu2$nmf==1],19) #
t2<-sample(rownames(nmfclu2)[nmfclu2$nmf==2],24)   ##
t3<-sample(rownames(nmfclu2)[nmfclu2$nmf==3],21) ##
t4<-sample(rownames(nmfclu2)[nmfclu2$nmf==4],21) ### tr1<-setdiff(rownames(nmfclu2)[nmfclu2$nmf==1],t1)
tr2<-setdiff(rownames(nmfclu2)[nmfclu2$nmf==2],t2)
tr3<-setdiff(rownames(nmfclu2)[nmfclu2$nmf==3],t3)
tr4<-setdiff(rownames(nmfclu2)[nmfclu2$nmf==4],t4)

### the feature selection is conducted on training data set
nsel=3000
datt.allgbm.cv3 = datt.allgbm[1:nsel,]

training <-datt.allgbm.cv3[,c(tr1,tr2,tr3,tr4)]
testing  <-datt.allgbm.cv3[,c(t1,t2,t3,t4)]

############################################### equal frequency
data discretization numbin=20 x<-t(training)
y<-nmfclu2[rownames(x),]
y<-as.factor(y)
 # value matrix
x<-apply(x,2,as.numeric)
x<-apply(x,2,rank)
xbin<-NULL
for (i in 1:dim(x)[2]) {
        temp<-cut(x[,i],breaks=numbin)
        temp<-as.numeric(temp)
)
        xbin<-cbind(xbin,temp)
}
colnames(xbin)<-colnames(x)
rownames(xbin)<-rownames(x)

######### end of discretization
```

Figure 16A

```
library(varSelRF)

#set.seed(1262118388.71279)
set.seed(24567)
rf <- varSelRF(xbin, y, ntree = 3000, ntreeIterat = 2000,
vars.drop.frac = 0.2, whole.range = TRUE,keep.forest = TRUE)
```

Figure 16A (continued)

```
loading required R packages
library(gplots)
library(cluster)

library(NMF)
library(survival)

##################################### Estimating the rank of
the data nsel <- 1600  ## the number of transcripts used for nmf clustering
datt.allgbm.cv3 = datt.allgbm[1:nsel,]  ###datt.allgbm is a data
matrix with rows indicating transcripts and column indicating samples.
#All the transcripts are sorted in descending order by cv values after
correlated ones filtered out.

datt.nmf=datt.allgbm.cv3 - min(datt.allgbm.cv3 )
estim.datt <- nmfEstimateRank(datt.nmf, range=2:7, nrun=100)

################### nmf clustering with 4 groups
res2all<-nmf(datt.nmf,4,nrun=50)
h2all <- coef(res2all)
nmfclu2<-apply(h2all,2,which.max) ## the clustering label for each
sample

####################################################################
Silhouette plot
eu.dist = as.dist(1-cor(datt.nmf))
sil.temp=silhouette(nmfclu2, eu.dist,)

lsams<-names(nmfclu2)[sil.temp[,3]>0] ## all the samples with positive
silhouette width nmfclu2<-as.data.frame(nmfclu2)
nmfclu2<-nmfclu2[lsams,,drop=FALSE]
colnames(nmfclu2)[1]<-"nmf"
table(nmfclu2$nmf)
```

Figure 16B

METHODS AND COMPOSITIONS FOR DIAGNOSIS OF GLIOBLASTOMA OR A SUBTYPE THEREOF

CROSS-REFERENCE TO RELATED APPLICATIONS

This application is a national stage of International Patent Application No. PCT/US2014/032966, filed Apr. 4, 2014, which claims the benefit of the priority of U.S. Provisional Patent Application No. 61/937,215, filed Feb. 7, 2014 and U.S. Provisional Patent Application No. 61/808,878, filed Apr. 5, 2013, which priority applications are incorporated herein by reference.

This invention was made with government support under grant Nos. P01LM011297 and P30CA010815 awarded by the National Institutes of Health. The government has certain rights in the invention.

SEQUENCE LISTING

Applicants hereby incorporates by reference the Sequence Listing material filed in electronic form herewith. This file is labeled WST141PCT_ST25.txt and contains 41,053 kb.

BACKGROUND OF THE INVENTION

Glioblastoma multiforme (GBM) are the most heterogeneous and lethal of the malignant adult brain tumors. Even with aggressive combination therapies, the prognosis of GBM remains dismal, with median survival of 15 months after diagnosis.[1]

Molecular classification of tumors is essential for developing personalized therapies. Although four distinct molecular subtypes have been identified by gene expression-based molecular classification of TCGA samples (i.e., Proneural (PN), Neural (N), Mesenchymal (M) and Classical (C))[3,4,33] the prognostic value of this stratification is weak and these subtypes contribute very little to the survival and prognostic stratification of GBMs.

Gene-level analysis of GBM has provided certain prospective gene signatures for the identification of GBM[3,4,28, 33-36]. For example, an 840-gene signature to predict the GBM subtypes was developed by the TCGA network,[3] but it is not yet translated to clinical practice. Despite considerable effort, no clinical diagnostic test for GBM subtyping is currently available.

SUMMARY OF THE INVENTION

In response to the urgent need in the art, the methods and compositions described herein provide an isoform-level expression signature that is useful in identifying novel molecular markers, as well as a more robust, reliable and clinically translatable genome-based diagnostic assay for improved clinical management of GBM patients, and GBM patient stratification useful to predict the molecular subtype of a GBM patient.

In one aspect, an isoform-level gene transcript panel is provided that can accurately classify a glioblastoma multiforme (GBM) subtype from a tumor sample.

In another aspect, a diagnostic reagent is provided that comprises the isoform level gene transcript panel of Table 1 or fragments thereof immobilized on a substrate, such as a microarray, a microfluidics card, a chip, a bead, or a chamber.

In yet a further aspect, a diagnostic reagent comprises a ligand capable of specifically complexing with, binding to, or quantitatively detecting or identifying a single target isoform transcript selected from the isoform transcripts of Table 1.

In another aspect, a kit, panel or microarray is provided, which comprises multiple such reagents, wherein at least one ligand is associated with a detectable label or with a substrate. In one embodiment, each reagent or ligand identifies the level of expression or activity of a different target isoform transcript of Table 1. In another embodiment, the, kit, panel or microarray comprises reagents that identify the level of expression or activity of all 121 "classifier" target isoform transcripts of Table 1. In another embodiment, the, kit, panel or microarray comprises reagents that identify the level of expression or activity of all 214 target isoform transcripts of Table 1. In a further embodiment, the kit, panel or microarray further comprises a ligand capable of specifically complexing with, binding to, or quantitatively detecting or identifying a control (upregulated or downregulated relative to normal) isoform transcript and/or a housekeeping gene or endogenous controls identified in Table 1. In still another embodiment, the kit, panel or microarray further comprises a ligand capable of specifically complexing with, binding to, or quantitatively detecting or identifying all of the isoform transcripts and controls identified in Table 1. In one embodiment, the ligand is an oligonucleotide sequence of about 20 nucleotides for use as a PCR primer or a pair of oligonucleotide sequences that form a primer pair or a labeled probe. Each primer or primer pair or probe in the kit, panel or microarray hybridizes to one of the isoform transcripts in Table 1.

In another aspect, the reagent, kit, panel or microarray further comprises computer software that performs the functions described in the flowchart of FIG. 8.

In yet another aspect, an isoform-level assay for diagnosis of the molecular subtype of a glioblastoma in a subject is provided. The assay comprises assaying a sample obtained from a subject that has or is suspected of having a glioblastoma by contacting the sample with an isoform transcript panel of Table 1 or a reagent, kit, panel or microarray of ligands capable of specifically complexing with, binding to, or quantitatively detecting or identifying the level or activity of target isoform transcripts selected from the isoforms of Table 1. In one aspect, this assaying step involves performing an RT-qPCR assay with ligands, e.g., PCR primer sets, and/or labeled probes directed to each target isoform transcript and controls identified in Table 1. The individual expression levels or activities of the target isoform transcripts relative to a reference standard are then analyzed in a program that performs the algorithms and functions of FIG. 8. This program then generates an isoform transcript signature that permits a diagnosis or prediction of that subject's GBM molecular subtype.

In one embodiment, this process is performed by a computer processor or computer-programmed instrument that generates numerical or graphical data useful in the diagnosis of the condition using the algorithms identified in FIG. 8.

In a further aspect, a computer program or source code is provided that performs the functions and uses the algorithm structure of the flow chart of FIG. 8.

Other aspects and advantages of these compositions and methods are described further in the following detailed description of the preferred embodiments thereof.

BRIEF DESCRIPTION OF THE DRAWINGS

FIG. 1A is a Kaplan-Meier survival curve for the overlapping TCGA study isoform-based core samples (169 GBM patients).

FIG. 1B is a Kaplan-Meier survival curves for the overlapping TCGA study core gene-based samples (169 GBM patients).

FIG. 2 is an isoform-based core samples from TCGA (342 GBM patients) belonging to the four subtypes identified as Proneural (PN), Neural (N), Mesenchymal (M) or Classical (C). The statistical significance of the overall plot and that of one-to-one comparison for each subtype is shown. The number of patients surviving for different time periods is also indicated below the survival plots.

FIG. 3A, having a left graph and a right graph, shows the development of an isoform/transcript-based classifier and its validation. The out-of-bag (OOB) error rate was plotted for a gene-based (left graph) and isoform-based (right graph) classifier model, where the x-axis denotes the number of variables or features and the y-axis represents the OOB error rate. The blue line forming a box in the left corner of each graph shows the OOB error rate for 50 features in each model, and the horizontal line depicts the lowest error rate achievable by the two models.

FIG. 3B is a graph showing the correlation of expression estimates obtained on two different cohorts of GBM patients on two different platforms. The x-axis represents the mean fold change for 121 transcripts/isoforms based on exon-array data for isoform-based core samples from TCGA, and the y-axis shows the mean fold change for the same transcripts/isoforms for Penn cohort of GBM patients based on RT-qPCR analysis. Both sets of data are $\log_2$ transformed. The equation for the linear relationship and the $R^2$ represented on the figure were calculated after removing the outliers.

FIG. 3C are five boxplots representing the expression as fold change of the indicated marker genes for the four different subtypes in each subtype of Penn cohort of GBM patients identified by the 121 isoform classifier of Table 1. For analysis of marker gene expression, the algorithm was applied by excluding these gene expression estimates from the classifier. Two out of 206 samples that changed classes were omitted from the boxplot analysis. The y-axis for NES and MET are shown in logarithmic scale. All fold changes were calculated relative to normal brain tissue.

FIG. 16A shows the R script as text files for the PIGEx-Class classification system data discretization feature.

FIG. 16B shows the R script as text files for the PIGEx-Class classification system NMF clustering feature.

DETAILED DESCRIPTION OF THE INVENTION

Figure 4A:
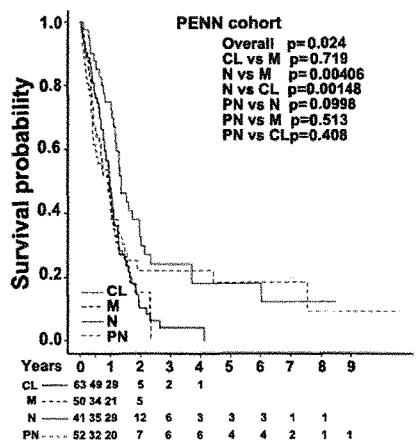
FIG. 4A is a Kaplan-Meier survival plot for Penn cohort of GBM patients with the overall survival curve for GBM patients who were classified into four subtypes by the 121 isoform classifier based on the RT-qPCR expression estimates. The statistical significance of each plot is indicated.

The complexity of the gene structure in the human genome and the importance of using alternative splice variants as molecular signatures towards genomic medicine are increasingly appreciated.[29-31] Alternative splicing is a commonly used molecular strategy for creating multiple gene isoforms and many of the isoforms produced in this manner are tightly regulated during normal development but are mis-regulated in cancer cells.[7,32] Using The Cancer Genome Atlas (TCGA) exon-array data, the inventors developed an isoform-level gene panel that could accurately classify the four GBM subtypes and isoform-level assay for using in the diagnosis of the subtypes of GBM. To the best of the inventors' knowledge, this is the first isoform-level assay for efficient molecular stratification of cancer. The isoform-level analysis described herein lead to a substantially better subtype prediction model than the gene-level analysus[3,4,28,33-36] in terms of improved classification accuracy, fewer numbers of variables (isoforms) in the final model, and statistically significant prognostic stratification of the refined subtypes. In contrast to the TCGA 840 gene signature for GBM, the inventor's isoform-based classifier can predict the GBM subtype with high accuracy using a much smaller gene panel (e.g., between 121 to 214 isoform transcripts), which was successfully transformed to an RT-qPCR-based assay.[37] The isoform-level classifiers and assay methods described herein provide a quantitative and reproducible diagnosis of GBM molecular subtypes, a requirement towards personalized medicine.

I. DEFINITIONS AND COMPONENTS OF THE COMPOSITIONS AND METHODS

"Patient" or "subject" as used herein means a mammalian animal, including a human, a veterinary or farm animal, a domestic animal or pet, and animals normally used for clinical research. In one embodiment, the subject of these methods and compositions is a human.

By "isoform" is meant an alternative expression product or variant of a single gene in a given species, including forms generated by alternative splicing, single nucleotide polymorphisms, alternative promoter usage, alternative translation initiation small genetic differences between alleles of the same gene. Genes produce alternative gene products through the usage of alternative promoters during development. Alternative gene isoforms display opposing expression patterns, nullifying the expression changes at the gene level. Frequently this expression pattern is reversed back in disease conditions of adult brain. Thus the target isoforms identified in Table 1 provide targets for the detection of brain disease, such as GMB.

By "target isoform" or "target isoform signature" as used herein is meant a single nucleotide acid sequence, e.g., RNA which the inventors have determined is useful as a classifier of GMB subtypes. The inventors have identified target isoform transcripts using in the GBM classifier as including the 121 isoform transcripts and corresponding genes listed in Table 1 and including the 93 isoform transcripts in the lower portion of Table 1. Throughout this specification, wherever the term target isoform transcript or combination of target isoform transcripts is used, it should be understood that the target isoform transcripts can be any of those identified in Table 1. The target isoforms may be combined to form sets of classifiers in the methods and diagnostic reagents described herein. In one embodiment, it is understood that all molecular forms useful in this context are physiological, e.g., naturally occurring in the species. The gene or transcript sequences are publically available. For example, they can be identified in the ENSEMBL database which is publically available as version 56 Alternatively, the transcripts are publically available from the UCSC Genome Browser version hg19 (see, e.g. Kent W J et al, "The human genome browser at UCSC." Genome Res., 2002 June; 12(6):996-1006).

TABLE 1

| ENSEMBL ENST# TRANSCRIPT ID/ (SEQ ID NO:) | GENE NAME or SYMBOL | CHRO-MOSOME # | NUCL. BASE START | NUCL BASE END | STRAND | ENSEMBL GENE ID (ENSG#) |
|---|---|---|---|---|---|---|
| ISOFORM TARGETS FORMING 121 ISOFORM SIGNATURE\ FOR DIAGNOSIS OF GMB ||||||||
| 00000276681 SEQ ID NO: 1 | MAL2 | 8 | 120220610 | 120257909 | 1 | 00000147676 |
| 00000467088 SEQ ID NO: 2 | CTTNBP2 | 7 | 117400322 | 117407245 | −1 | 00000077063 |
| 00000381158 SEQ ID NO: 3 | RAB3C | 5 | 57913336 | 58147405 | 1 | 00000152932 |
| 00000334389 SEQ ID NO: 4 | AL390816.1 | 14 | 62584075 | 62595132 | 1 | 00000186369 |
| 00000495883 SEQ ID NO: 5 | SNAP25 | 20 | 10276878 | 10288066 | 1 | 00000132639 |
| 00000470756 SEQ ID NO: 6 | ALCAM | 3 | 105085762 | 105244237 | 1 | 00000170017 |
| 00000378383 SEQ ID NO: 7 | FNDC3A | 13 | 49550205 | 49720983 | 1 | 00000102531 |

TABLE 1-continued

| ENSEMBL ENST# TRANSCRIPT ID/ (SEQ ID NO:) | GENE NAME or SYMBOL | CHROMOSOME # | NUCL. BASE START | NUCL BASE END | STRAND | ENSEMBL GENE ID (ENSG#) |
|---|---|---|---|---|---|---|
| 00000497227 SEQ ID NO: 8 | LRRC16A | 6 | 25465764 | 25472859 | 1 | 00000079691 |
| 00000463206 SEQ ID NO: 9 | PPAPR3 | 9 | 104032084 | 104075176 | 1 | 00000148123 |
| 00000498732 SEQ ID NO: 10 | RP1-177G6 | X | 139791945 | 139854839 | 1 | 00000203930 |
| 00000489023 SEQ ID NO: 11 | C2orf21 | 2 | 210693953 | 210835038 | 1 | 00000144406 |
| 00000425974 SEQ ID NO: 12 | AC064875.1 | 2 | 13106910 | 13147138 | −1 | 00000225649 |
| 00000424518 SEQ ID NO: 13 | HOTAIR | 12 | 54356092 | 54368740 | −1 | |
| 00000272644 SEQ ID NO: 14 | GPR17 | 2 | 128403747 | 128410213 | 1 | 00000144230 |
| 00000342358 SEQ ID NO: 15 | ATP13A5 | 3 | 192992579 | 193096632 | −1 | 00000187527 |
| 00000335523 SEQ ID NO: 16 | VSTM2B | 19 | 30017491 | 30054841 | 1 | 00000187135 |
| 00000020926 SEQ ID NO: 17 | SYT13 | 11 | 45261853 | 45307884 | −1 | 00000019505 |
| 00000180173 SEQ ID NO: 18 | MTMR7 | 8 | 17155552 | 17270836 | −1 | 00000003987 |
| 00000359598 SEQ ID NO: 135 | ELAVL2 | 9 | 23692025 | 23765104 | −1 | 00000107105 |
| 00000408006 SEQ ID NO: 136 | KLRK1 | 12 | 10598642 | 10602299 | −1 | 00000134545 |
| 00000437025 SEQ ID NO: 19 | GABRA1 | 5 | 161275542 | 161326965 | 1 | 00000022355 |
| 00000328405 SEQ ID NO: 20 | KCNH8 | 3 | 19189946 | 19577138 | 1 | 00000183960 |
| 00000436393 SEQ ID NO: 21 | AC107933.1 | 8 | 105080740 | 105161076 | 1 | 00000225388 |
| 00000311812 SEQ ID NO: 22 | SNX31 | 8 | 101585116 | 101661893 | −1 | 00000174226 |
| 00000378993 SEQ ID NO: 23 | IL1RAPL1 | X | 28605516 | 29974840 | 1 | 00000169306 |
| 00000233946 SEQ ID NO: 31 | IL1R1 | 2 | 102770402 | 102796334 | 1 | 00000115594 |
| 00000393845 SEQ ID NO: 32 | WDR52 | 3 | 113010404 | 113160340 | −1 | 00000206530 |
| 00000448418 SEQ ID NO: 33 | MPPED2 | 11 | 30406040 | 30607930 | −1 | 00000066382 |
| 00000341752 SEQ ID NO: 34 | ANKS1B | 12 | 99137996 | 99225920 | −1 | 00000185046 |
| 00000374778 SEQ ID NO: 35 | AP000843.1 | 11 | 132290087 | 133402219 | −1 | 00000183715 |
| 00000303177 SEQ ID NO: 36 | AC093310 | 5 | 173472663 | 173536189 | 1 | 00000170091 |
| 00000483004 SEQ ID NO: 37 | CFB | 6 | 31916733 | 31919830 | 1 | 00000243649 |
| 00000427482 SEQ ID NO: 38 | SH3GL3 | 15 | 84115980 | 84287495 | 1 | 00000140600 |
| 00000358763 SEQ ID NO: 39 | SYN3 | 22 | 32908539 | 33454358 | −1 | 00000185666 |
| 00000444190 SEQ ID NO: 40 | ARPP-21 | 3 | 35682456 | 35835949 | 1 | 00000172995 |
| 00000331565 SEQ ID NO: 41 | SLC6A17 | 1 | 110693108 | 110744824 | 1 | 00000197106 |
| 00000351273 SEQ ID NO: 42 | ACPP | 3 | 132036251 | 132087142 | 1 | 00000014257 |
| 00000414552 SEQ ID NO: 43 | GABRG2 | 5 | 161494648 | 161582545 | 1 | 00000113327 |
| 00000328439 SEQ ID NO: 44 | MYT1 | 20 | 62795827 | 62873604 | 1 | 00000196132 |
| 00000361727 SEQ ID NO: 45 | CNTNAP2 | 7 | 145813453 | 148118090 | 1 | 00000174469 |
| 00000356915 + 00000371988 SEQ ID NO: 46 | DCX | X | 110537007 | 110655406 | −1 | 00000077279 |
| 00000330884 SEQ ID NO: 47 | SULT4A1 | 22 | 44220389 | 44258383 | −1 | 00000130540 |
| 00000260227 SEQ ID NO: 48 | MMP7 | 11 | 102391268 | 102401458 | −1 | 00000137673 |

TABLE 1-continued

| ENSEMBL ENST# TRANSCRIPT ID/ (SEQ ID NO:) | GENE NAME or SYMBOL | CHRO-MOSOME # | NUCL. BASE START | NUCL BASE END | STRAND | ENSEMBL GENE ID (ENSG#) |
|---|---|---|---|---|---|---|
| 00000281156 SEQ ID NO: 49 | KHDRBS2 | 6 | 62390139 | 62996132 | −1 | 00000112232 |
| 00000350228 SEQ ID NO: 50 | KCNC2 | 12 | 75433896 | 75603511 | −1 | 00000166006 |
| 00000342916 SEQ ID NO: 51 | EGFR | 7 | 55086725 | 55236328 | 1 | 00000146648 |
| 00000354078 SEQ ID NO: 52 | MAL | 2 | 95691538 | 95719737 | 1 | 00000172005 |
| 00000303230 SEQ ID NO: 53 | HCN1 | 5 | 45259349 | 45696253 | −1 | 00000164588 |
| 00000334005 SEQ ID NO: 54 | PLCB4 | 20 | 9076932 | 9461460 | 1 | 00000101333 |
| 00000439649 SEQ ID NO: 55 | GFRA1 | 10 | 117816444 | 118032796 | −1 | 00000151892 |
| 00000392314 SEQ ID NO: 56 | TMEFF2 | 2 | 192813769 | 193059642 | −1 | 00000144339 |
| 00000439399 SEQ ID NO: 57 | SNAP91 | 6 | 84262607 | 84419127 | −1 | 00000065609 |
| 00000404301 SEQ ID NO: 58 | RGS6 | 14 | 72431509 | 73006978 | 1 | 00000182732 |
| 00000310157 + 00000424910 SEQ ID NO: 59 | KLK6 | 19 | 51461888 | 51472929 | −1 | 00000167755 |
| 00000219746 SEQ ID NO: 60 | TOX3 | 16 | 52471918 | 52580635 | −1 | 00000103460 |
| 00000357277 SEQ ID NO: 61 | REPS2 | X | 16964814 | 17171395 | 1 | 00000169891 |
| 00000370603 + 00000441825 SEQ ID NO: 62 | FGF13 | X | 137713740 | 138067246 | −1 | 00000129682 |
| 00000453976 SEQ ID NO: 63 | RIMS1 | 6 | 72960033 | 73112507 | 1 | 00000079841 |
| 00000215939 SEQ ID NO: 64 | CRYBB1 | 22 | 26995242 | 27014052 | −1 | 00000100122 |
| 00000262624 SEQ ID NO: 65 | MAG | 19 | 35783028 | 35804707 | 1 | 00000105695 |
| 00000285273 SEQ ID NO: 66 | CA10 | 17 | 49707675 | 50237161 | −1 | 00000154975 |
| 00000373434 SEQ ID NO: 67 | RALGPS1 | 9 | 129724504 | 129980091 | 1 | 00000136828 |
| 00000373965 + 00000414778 + 00000455746 SEQ ID NO: 68 | PCDH15 | 10 | 55562531 | 56561051 | −1 | 00000150275 |
| 00000370859 SEQ ID NO: 69 | SLC44A5 | 1 | 75667816 | 76076801 | −1 | 00000137968 |
| 00000299222 SEQ ID NO: 70 | AC079953.2 | 12 | 101188735 | 101522114 | 1 | 00000151572 |
| 00000492720 SEQ ID NO: 71 | DENND2A | 7 | 140243378 | 140305606 | −1 | 00000146966 |
| 00000294696 SEQ ID NO: 72 | HFM1 | 1 | 91726324 | 91870426 | −1 | 00000162669 |
| 00000424189 SEQ ID NO: 73 | DGKI | 7 | 137075270 | 137531838 | −1 | 00000157680 |
| 00000376888 SEQ ID NO: 74 | MOG | 6 | 29624780 | 29639888 | 1 | 00000204655 |
| 00000382275 SEQ ID NO: 75 | CDH18 | 5 | 19473141 | 19988339 | −1 | 00000145526 |
| 00000397752 SEQ ID NO: 76 | MET | 7 | 116312446 | 116438440 | 1 | 00000105976 |
| 00000453617 SEQ ID NO: 77 | NPNT | 4 | 106816605 | 106892824 | 1 | 00000168743 |
| 00000343508 SEQ ID NO: 78 | CSMD3 | 8 | 113235157 | 114389382 | −1 | 00000164796 |
| 00000373380 SEQ ID NO: 24 | CSMD2 | 1 | 34057407 | 34175104 | −1 | 00000121904 |
| 00000361655 + 00000395337 SEQ ID NO: 25 | PCDH11X | X | 91034304 | 91139006 | 1 | 00000102290 |
| 00000394755 SEQ ID NO: 26 | EVI2A | 17 | 29644676 | 29648717 | −1 | 00000126860 |
| 00000477310 SEQ ID NO: 27 | XXbac-BPG116M5 | 6 | 31895501 | 31919807 | 1 | 00000244255 |

TABLE 1-continued

| ENSEMBL ENST# TRANSCRIPT ID/ (SEQ ID NO:) | GENE NAME or SYMBOL | CHROMOSOME # | NUCL. BASE START | NUCL BASE END | STRAND | ENSEMBL GENE ID (ENSG#) |
|---|---|---|---|---|---|---|
| 00000495831 SEQ ID NO: 28 | MYO1G | 7 | 45002261 | 45018668 | −1 | 00000136286 |
| 00000358671 SEQ ID NO: 29 | FCGR2B | 1 | 161632951 | 161648444 | 1 | 00000072694 |
| 00000260126 SEQ ID NO: 30 | SLCO5A1 | 8 | 70584575 | 70747208 | −1 | 00000137571 |
| 00000256183 + 00000444303 SEQ ID NO: 133 | AMPD3 | 11 | 10472224 | 10529126 | 1 | 00000133805 |
| 00000375773 SEQ ID NO: 132 | KYNU | 2 | 143635226 | 143747106 | 1 | 00000115919 |
| 00000396023 SEQ ID NO: 131 | CRYM | 16 | 21269843 | 21289657 | −1 | 00000103316 |
| 00000435105 SEQ ID NO: 137 | FMOD | 1 | 203309753 | 203317340 | −1 | 00000122176 |
| 00000366621 SEQ ID NO: 130 | KCNK1 | 1 | 233749750 | 233808258 | 1 | 00000135750 |
| 00000370314 SEQ ID NO: 129 | GABRA3 | X | 151334706 | 151619830 | −1 | 00000011677 |
| 00000375108 SEQ ID NO: 128 | PLA2G5 | 1 | 20396701 | 20417661 | 1 | 00000127472 |
| 00000266674 SEQ ID NO: 127 | LGR5 | 12 | 71833813 | 71978622 | 1 | 00000139292 |
| 00000354567 + 00000370806 SEQ ID NO: 126 | AK5 | 1 | 77747736 | 78025650 | 1 | 00000154027 |
| 00000240618 SEQ ID NO: 125 | AC022075.1 | 12 | 10524953 | 10542640 | −1 | 00000213809 |
| 00000262095 + 00000491143 SEQ ID NO: 124 | ONECUT2 | 18 | 55102917 | 55158529 | 1 | 00000119547 |
| 00000273450 SEQ ID NO: 123 | ALDH1L1 | 3 | 125822412 | 125900029 | −1 | 00000144908 |
| 00000357742 SEQ ID NO: 122 | MCTP2 | 15 | 94774951 | 95023632 | 1 | 00000140563 |
| 00000404234 SEQ ID NO: 121 | SEZ6L | 22 | 26565440 | 26776437 | 1 | 00000100095 |
| 00000254765 SEQ ID NO: 120 | POPDC3 | 6 | 105606155 | 105627735 | −1 | 00000132429 |
| 00000217305 SEQ ID NO: 119 | PDYN | 20 | 1959405 | 1974703 | −1 | 00000101327 |
| 00000393913 SEQ ID NO: 118 | FAM176A | 2 | 75719444 | 75788039 | −1 | 00000115363 |
| 00000400457 SEQ ID NO: 117 | PCDH11Y | Y | 4924930 | 5610265 | 1 | 00000099715 |
| 00000380032 SEQ ID NO: 116 | C9orf11 | 9 | 27284659 | 27297137 | −1 | 00000120160 |
| 00000263665 SEQ ID NO: 115 | CNTN3 | 3 | 74311719 | 74570291 | −1 | 00000113805 |
| 00000332191 SEQ ID NO: 114 | ROBO2 | 3 | 77089881 | 77696267 | 1 | 00000185008 |
| 00000396884 SEQ ID NO: 113 | SOX10 | 22 | 38368307 | 38380544 | −1 | 00000100146 |
| 00000382622 SEQ ID NO: 112 | PRMT8 | 12 | 3600402 | 3703139 | 1 | 00000111218 |
| 00000370103 SEQ ID NO: 111 | OLFM3 | 1 | 102268130 | 102462586 | −1 | 00000118733 |
| 00000285105 SEQ ID NO: 134 | AIM1 | 6 | 106989093 | 107018335 | 1 | 00000112297 |
| 00000425955 + 00000458628 SEQ ID NO: 110 | CXorf35 | X | 100740462 | 100788446 | 1 | 00000196440 |
| 00000420628 SEQ ID NO: 109 | MMP19 | 12 | 56229244 | 56236735 | −1 | 00000123342 |
| 00000367053 SEQ ID NO: 108 | CR1 | 1 | 207669502 | 207813992 | 1 | 00000203710 |
| 00000264318 SEQ ID NO: 107 | GABRA4 | 4 | 46920917 | 46996424 | −1 | 00000109158 |
| 00000416284 SEQ ID NO: 106 | FAM19A2 | 12 | 62102045 | 62261212 | −1 | 00000198673 |
| 00000399232 SEQ ID NO: 105 | MDGA2 | 14 | 47309295 | 48143953 | −1 | 00000139915 |
| 00000376447 SEQ ID NO: 104 | RASEF | 9 | 85594500 | 85678043 | −1 | 00000165105 |

TABLE 1-continued

| ENSEMBL ENST# TRANSCRIPT ID/ (SEQ ID NO:) | GENE NAME or SYMBOL | CHRO- MOSOME # | NUCL. BASE START | NUCL BASE END | STRAND | ENSEMBL GENE ID (ENSG#) |
|---|---|---|---|---|---|---|
| 00000216492 SEQ ID NO: 103 | CHGA | 14 | 93389445 | 93401636 | 1 | 00000100604 |
| 00000369261 SEQ ID NO: 102 | KLHL32 | 6 | 97372605 | 97588630 | 1 | 00000186231 |
| 00000369574 SEQ ID NO: 101 | C6orf163 | 6 | 88054600 | 88075181 | 1 | 00000203872 |
| 00000379959 SEQ ID NO: 100 | IL2RA | 10 | 6052652 | 6104288 | −1 | 00000134460 |
| 00000392441 SEQ ID NO: 99 | CCDC62 | 12 | 123259073 | 123311929 | 1 | 00000130783 |
| 00000457059 SEQ ID NO: 98 | DYNC1I1 | 7 | 95433596 | 95727311 | 1 | 00000158560 |
| 00000392825 SEQ ID NO: 97 | GALNT13 | 2 | 154728426 | 155310361 | 1 | 00000144278 |
| 00000259056 SEQ ID NO: 96 | GALNT5 | 2 | 158114110 | 158170723 | 1 | 00000136542 |
| 00000371015 SEQ ID NO: 95 | PHACTR3 | 20 | 58179603 | 58422766 | 1 | 00000087495 |
| CONTROL GENE/TRANSCRIPTS ON ASSAY UPREGULATED IN ALL GBM RELATIVE TO NORMAL | | | | | | |
| 00000373020 SEQ ID NO: 94 | TSPAN6 | | | | | |
| 00000218340 SEQ ID NO: 93 | RP2 | | | | | |
| 00000483967 SEQ ID NO: 92 | EZH2 | | | | | |
| 00000263635 SEQ ID NO: 90 | TANC1 | | | | | |
| 00000450318 SEQ ID NO: 89 | NUSAP1 | | | | | |
| 00000411739 SEQ ID NO: 88 | NEDD1 | | | | | |
| 00000478293 SEQ ID NO: 87 | MKI67 | | | | | |
| 00000295633 SEQ ID NO: 86 | FSTL1 | | | | | |
| CONTROL GENE/TRANSCRIPTS ON ASSAY DOWNREGULATED IN ALL GBM RELATIVE TO NORMAL | | | | | | |
| 00000389722 SEQ ID NO: 85 + 00000389723 SEQ ID NO: 91 | SPTB | | | | | |
| 00000381142 SEQ ID NO: 84 | TYRP1 | | | | | |
| 00000369777 SEQ ID NO: 83 | NEURL | | | | | |
| 00000414191 + 00000439163 SEQ ID NO: 82 | PLCH1 | | | | | |
| 00000262450 SEQ ID NO: 81 | CHD5 | | | | | |
| 00000322893 SEQ ID NO: 80 | KCNH5 | | | | | |
| 00000304045 SEQ ID NO: 79 | KLK7 | | | | | |
| ENDOGENOUS CONTROLS | | | | | | |
| | GAPDH | | | | | |
| | POLR2A* | *used for normali- zation | | | | |
| | B2M | | | | | |
| | ACTB | | | | | |
| ADDITIONAL ISOFORM TARGETS FORMING ADDITIONAL SIGNATURES FOR DIAGNOSIS OF GMB | | | | | | |
| 00000216775 SEQ ID NO: 138 | CPNE6 | 14 | 24540756 | 24547295 | 1 | 00000100884 |
| 00000219368 SEQ ID NO: 139 | FA2H | 16 | 74746853 | 74808730 | −1 | 00000103089 |

TABLE 1-continued

| ENSEMBL ENST# TRANSCRIPT ID/ (SEQ ID NO:) | GENE NAME or SYMBOL | CHRO- MOSOME # | NUCL. BASE START | NUCL BASE END | STRAND | ENSEMBL GENE ID (ENSG#) |
|---|---|---|---|---|---|---|
| 00000221485 SEQ ID NO: 140 | SLC17A7 | 19 | 49932656 | 49944808 | -1 | 00000104888 |
| 00000225441 SEQ ID NO: 141 | RUNDC3A | 17 | 42385927 | 42395237 | 1 | 00000108309 |
| 00000242315 SEQ ID NO: 142 | KIAA1045 | 9 | 34958321 | 34982541 | 1 | 00000122733 |
| 00000256178 SEQ ID NO: 143 | LYVE1 | 11 | 10579413 | 10590365 | -1 | 00000133800 |
| 00000260795 SEQ ID NO: 144 | FGFR3 | 4 | 1795560 | 1810598 | 1 | 00000068078 |
| 00000261592 SEQ ID NO: 145 | NOL4 | 18 | 31431064 | 31803515 | -1 | 00000101746 |
| 00000262545 SEQ ID NO: 146 | PCSK2 | 20 | 17207636 | 17465223 | 1 | 00000125851 |
| 00000263050 SEQ ID NO: 147 | AKAP7 | 6 | 131571623 | 131604675 | 1 | 00000118507 |
| 00000263464 SEQ ID NO: 148 | BIRC3 | 11 | 102188194 | 102208448 | 1 | 00000023445 |
| 00000285274 SEQ ID NO: 149 | FOXO3B | 17 | 18565250 | 18585572 | -1 | 00000213688 |
| 00000288221 SEQ ID NO: 150 | ERC2 | 3 | 55542336 | 56502391 | -1 | 00000187672 |
| 00000302102 SEQ ID NO: 151 | ATP1A3 | 19 | 42470734 | 42498379 | -1 | 00000105409 |
| 00000303115 SEQ ID NO: 152 | IL7R | 5 | 35857000 | 35879705 | 1 | 00000168685 |
| 00000306317 SEQ ID NO: 153 | LGI3 | 8 | 22004338 | 22014345 | -1 | 00000168481 |
| 00000309384 SEQ ID NO: 154 | KLRC4 | 12 | 10559983 | 10562356 | -1 | 00000183542 |
| 00000311854 + 00000380781 SEQ ID NO: 155 | NEFL | 8 | 24808480 | 24814131 | -1 | 00000104725 |
| 00000315947 SEQ ID NO: 156 | OR4N2 | 14 | 20295608 | 20296531 | 1 | 00000176294 |
| 00000327305 SEQ ID NO: 157 | NETO1 | 18 | 70409671 | 70535184 | -1 | 00000166342 |
| 00000333447 SEQ ID NO: 158 | PPFIA2 | 12 | 81653356 | 81851648 | -1 | 00000139220 |
| 00000350485 SEQ ID NO: 159 | TAC1 | 7 | 97361396 | 97369750 | 1 | 00000006128 |
| 00000356921 + 00000358407 + 00000381269 SEQ ID NO: 160 | SLC8A3 | 14 | 70510934 | 70655787 | -1 | 00000100678 |
| 00000367397 SEQ ID NO: 161 | CRB1 | 1 | 197382959 | 197413949 | 1 | 00000134376 |
| 00000367733 SEQ ID NO: 162 | DNM3 | 1 | 171810638 | 172102530 | 1 | 00000197959 |
| 00000370056 SEQ ID NO: 163 | VAV3 | 1 | 108113782 | 108507585 | -1 | 00000134215 |
| 00000371194 SEQ ID NO: 164 | AL590244.1 | 6 | 49518388 | 49529620 | 1 | 00000197261 |
| 00000373970 SEQ ID NO: 165 | DKK1 | 10 | 54074056 | 54077417 | 1 | 00000107984 |
| 00000374848 SEQ ID NO: 166 | C9orf125 | 9 | 104235453 | 104249475 | -1 | 00000165152 |
| 00000377899 SEQ ID NO: 167 | PCSK2 | 20 | 17206752 | 17465223 | 1 | 00000125851 |
| 00000378122 SEQ ID NO: 168 | PCDHA9 | 5 | 140227357 | 140233515 | 1 | 00000204961 |
| 00000381055 SEQ ID NO: 169 | ADAMTS6 | 5 | 64444570 | 64777747 | -1 | 00000049192 |
| 00000381902 SEQ ID NO: 170 | KLRC2 | 12 | 10583210 | 10588592 | -1 | 00000205809 |
| 00000381904 SEQ ID NO: 171 | KLRC3 | 12 | 10564921 | 10573194 | -1 | 00000205810 |
| 00000389125 SEQ ID NO: 172 | GRIK1 | 21 | 30909254 | 31311943 | -1 | 00000171189 |
| 00000390237 SEQ ID NO: 173 | IGKC | 2 | 89156674 | 89157196 | -1 | 00000211592 |
| 00000390329 + 00000424688 SEQ ID NO: 174 | D87017.2 | 22 | 23261707 | 23262030 | 1 | 00000211683 |

TABLE 1-continued

| ENSEMBL ENST# TRANSCRIPT ID/ (SEQ ID NO:) | GENE NAME or SYMBOL | CHROMOSOME # | NUCL. BASE START | NUCL BASE END | STRAND | ENSEMBL GENE ID (ENSG#) |
|---|---|---|---|---|---|---|
| 00000390543 SEQ ID NO: 175 | IGHG4 | 14 | 106090687 | 106092403 | −1 | 00000211892 |
| 00000390545 SEQ ID NO: 176 | IGHG2 | 14 | 106109389 | 106111127 | −1 | 00000211893 |
| 00000390547 SEQ ID NO: 177 | IGHA1 | 14 | 106173457 | 106175002 | −1 | 00000211895 |
| 00000390549 SEQ ID NO: 178 | IGHM | 14 | 106207675 | 106209408 | −1 | 00000211896 |
| 00000393296 SEQ ID NO: 179 | SYT6 | 1 | 114631914 | 114696472 | −1 | 00000134207 |
| 00000398769 SEQ ID NO: 180 | AC008013.2 | 12 | 31265170 | 31272406 | −1 | 00000177359 |
| 00000400677 SEQ ID NO: 181 | HMX1 | 4 | 8868773 | 8873543 | −1 | 00000215612 |
| 00000406397 SEQ ID NO: 182 | VSNL1 | 2 | 17722427 | 17838285 | 1 | 00000163032 |
| 00000409748 SEQ ID NO: 183 | CNTNAP5 | 2 | 124782864 | 125672912 | 1 | 00000155052 |
| 00000411758 SEQ ID NO: 184 | AC008088.2 | 17 | 20294965 | 20319997 | 1 | 00000154898 |
| 00000413687 SEQ ID NO: 185 | C1orf106 | 1 | 200863999 | 200884863 | 1 | 00000163362 |
| 00000418923 SEQ ID NO: 186 | RP11-347N5 | 13 | 102945286 | 103054799 | −1 | 00000243319 |
| 00000421686 SEQ ID NO: 187 | RP11-146D12 | 9 | 42410363 | 42474269 | 1 | 00000240240 |
| 00000425271 SEQ ID NO: 188 | AL390115.1 | 1 | 166304121 | 166304999 | 1 | 00000229588 |
| 00000425633 SEQ ID NO: 189 | NCRNA00032 | 9 | 27245682 | 27282791 | −1 | 00000231459 |
| 00000425669 SEQ ID NO: 190 | AL450364.1 | 10 | 18802044 | 18834580 | −1 | 00000240291 |
| 00000427239 SEQ ID NO: 191 | COL11A1 | 1 | 103474029 | 103573734 | −1 | 00000060718 |
| 00000433011 SEQ ID NO: 192 | CXorf35 | X | 100673275 | 100788446 | 1 | 00000196440 |
| 00000434347 SEQ ID NO: 193 | SH3GL3 | 15 | 84159586 | 84287491 | 1 | 00000140600 |
| 00000436075 SEQ ID NO: 194 | AC007731.3 | 22 | 20837102 | 20838392 | −1 | 00000236670 |
| 00000437534 SEQ ID NO: 195 | CKMT1B | 15 | 43886225 | 43891604 | 1 | 00000237289 |
| 00000438418 SEQ ID NO: 196 | AC105765.2 | 3 | 18504392 | 18505831 | 1 | 00000228956 |
| 00000439543 SEQ ID NO: 197 | EMG1 | 12 | 7080087 | 7095921 | 1 | 00000126749 |
| 00000440363 SEQ ID NO: 198 | AF165176.1 | 21 | 41990433 | 42002693 | −1 | 00000233756 |
| 00000441231 SEQ ID NO: 199 | AL021406.1 | 20 | 8229351 | 8230389 | 1 | 00000225479 |
| 00000441301 SEQ ID NO: 200 | F13A1 | 6 | 6144311 | 6321128 | −1 | 00000124491 |
| 00000442176 SEQ ID NO: 201 | AC005550.1 | 7 | 15728003 | 15735116 | 1 | 00000229108 |
| 00000446737 SEQ ID NO: 202 | PAK3 | X | 110187513 | 110464146 | 1 | 00000077264 |
| 00000450146 SEQ ID NO: 203 | ERBB3 | 12 | 56492491 | 56497128 | 1 | 00000065361 |
| 00000454036 SEQ ID NO: 204 | SLC12A5 | 20 | 44650329 | 44688789 | 1 | 00000124140 |
| 00000457776 SEQ ID NO: 205 | RP11-423O2 | 1 | 142803532 | 142827235 | 1 | 00000232745 |
| 00000460438 SEQ ID NO: 206 | ETV1 | 7 | 13998382 | 14028728 | −1 | 00000006468 |
| 00000461801 SEQ ID NO: 207 | FXR1 | 3 | 180650824 | 180652984 | 1 | 00000114416 |
| 00000462598 SEQ ID NO: 208 | FYN | 6 | 112035550 | 112115053 | −1 | 00000010810 |
| 00000463645 SEQ ID NO: 209 | C2orf27A | 2 | 132491229 | 132509242 | 1 | 00000197927 |
| 00000464572 SEQ ID NO: 210 | FAM48A | 13 | 37612172 | 37633776 | −1 | 00000102710 |
| 00000466541 SEQ ID NO: 211 | SHROOM3 | 4 | 77357299 | 77480729 | 1 | 00000138771 |

TABLE 1-continued

| ENSEMBL ENST# TRANSCRIPT ID/ (SEQ ID NO:) | GENE NAME or SYMBOL | CHRO-MOSOME # | NUCL. BASE START | NUCL BASE END | STRAND | ENSEMBL GENE ID (ENSG#) |
|---|---|---|---|---|---|---|
| 00000468813 SEQ ID NO: 212 | CREB5 | 7 | 28763917 | 28766348 | 1 | 00000146592 |
| 00000470802 SEQ ID NO: 213 | ROBO2 | 3 | 77678273 | 77698651 | 1 | 00000185008 |
| 00000471090 SEQ ID NO: 214 | RP11-706O15 | X | 3735576 | 3742639 | −1 | 00000205664 |
| 00000473185 SEQ ID NO: 215 | CHI3L1 | 1 | 203148059 | 203151262 | −1 | 00000133048 |
| 00000473361 SEQ ID NO: 216 | SPOCD1 | 1 | 32256029 | 32264216 | −1 | 00000134668 |
| 00000473640 SEQ ID NO: 217 | ASTN1 | 1 | 176945189 | 177001686 | −1 | 00000152092 |
| 00000475285 SEQ ID NO: 218 | SLIT1 | 10 | 98912808 | 98924646 | −1 | 00000187122 |
| 00000475659 SEQ ID NO: 219 | CRB1 | 1 | 197237406 | 197327258 | 1 | 00000134376 |
| 00000478136 SEQ ID NO: 220 | FAM19A1 | 3 | 68053359 | 68594776 | 1 | 00000183662 |
| 00000478803 SEQ ID NO: 221 | PLA2G5 | 1 | 20396788 | 20417321 | 1 | 00000127472 |
| 00000479198 SEQ ID NO: 222 | SYNPR | 3 | 63429004 | 63602597 | 1 | 00000163630 |
| 00000480144 SEQ ID NO: 223 | SLTM | 15 | 59190181 | 59225799 | −1 | 00000137776 |
| 00000482437 SEQ ID NO: 224 | CCDC76 | 1 | 100598721 | 100610123 | 1 | 00000122435 |
| 00000486152 SEQ ID NO: 225 | ZBTB20 | 3 | 114106122 | 114219238 | −1 | 00000181722 |
| 00000490066 SEQ ID NO: 226 | SLC16A9 | 10 | 61443856 | 61469280 | −1 | 00000165449 |
| 00000490795 SEQ ID NO: 227 | PRKD1 | 14 | 30060321 | 30066874 | −1 | 00000184304 |
| 00000494864 SEQ ID NO: 228 | CYP1B1 | 2 | 38297209 | 38337044 | −1 | 00000138061 |
| 00000498168 SEQ ID NO: 229 | EXOSC7 | 3 | 45018584 | 45030734 | 1 | 00000075914 |
| 00000498203 SEQ ID NO: 230 | SPAG4 | 20 | 34205611 | 34208856 | 1 | 00000061656 |
| 00000498435 SEQ ID NO: 231 | AC110080.11 | 2 | 89512908 | 89513413 | −1 | 00000244575 |

By "classifier" or "signature" is meant the combination of target isoform transcripts useful to diagnose or predict the GBM subtype of disease in a tested patient or subject biological sample. For example, the 121 target isoform transcripts of Table 1 can be one signature (e.g., as used in the process disclosed in FIG. 8). Alternatively the 214 target isoform transcripts identified in total in Table 1 can be a classifier in a similar process. In another embodiment, some selection of target isoforms from Table 1 that are more than 121 but less than 214 may be used as the classifier. In still further embodiments, small numbers of target isoforms selected from the 214 or 121 of Table 1 may also be used as classifiers according to the methods and compositions described herein. In the context of the compositions and methods described herein, reference to "at least two," "at least five," at least 121" etc. of the isoform targets listed in any particular classifier set means any and all combinations of the target isoforms identified. Specific target isoforms for the isoform signature or classifier do not have to be in rank order as set out in Table 1.

The term "RNA-based assay" is intended to include, without limitation, assays such as RNA-seq or mRNA-seq assay by NextGen sequencing of RNA, or a customized microarray panel consisting of e.g., the 214 total transcripts or 121 "signature" transcripts of Table 1, or some combination thereof, plus controls, presented on e.g., AFFYME-TRIX exon-array; AGILENT microarray; ILLUMINE micro-array, also a NONOSTRING assay, ILLUMINA HISEQ assay or RT-qPCR based assay to measure the abundance of these isoform or gene transcripts. In one embodiment, RNA based assays are preferred for use in the methods described herein.

The methods and compositions described herein can, in principle, be translatable to known protein-based assays and ligands that bind proteins or peptides. However, as will be clear to one of skill in the art, if protein assays are used, such assays will not be useful for certain isoform transcripts in the classifiers that are non-coding (function as RNA and do not translate to protein).

By "significant change in expression" is meant an upregulation in the expression level of a nucleic acid sequence, e.g., genes or isoform, in comparison to the selected reference standard or control; a downregulation in the expression level of a nucleic acid sequence, e.g., genes or isoform transcript in comparison to the selected reference standard or control; or a combination of a pattern or relative pattern of certain upregulated and/or down regulated isoforms. The degree of change in isoform expression can vary with each individual.

The term "polynucleotide," when used in singular or plural form, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The term "polynucleotide" specifically includes cDNAs. The term includes DNAs (including cDNAs) and RNAs that contain one or more modified bases. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide of less than 20 bases, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

"Reference standard" as used herein refers to the source of the reference target isoform or gene levels. The "reference standard" is preferably provided by using the same assay technique as is used for measurement of the subject's target isoform levels in the reference subject or population, to avoid any error in standardization. The reference standard is, alternatively, a numerical value, a predetermined cutpoint, a mean, an average, a numerical mean or range of numerical means, a numerical pattern, a ratio, a graphical pattern or a gene signature profile or gene level profile derived from the same target isoform or target isoforms in a reference subject or reference population.

"Reference subject" or "Reference Population" defines the source of the reference standard. In one embodiment, the reference is a human subject or a population of subjects having no cancer, i.e., healthy controls or negative controls. In yet another embodiment, the reference is a human subject or population of subjects with one or more clinical indicators of GBM, but who did not develop GBM. In still another embodiment, the reference is a human subject or a population of subjects having benign brain nodules or cysts. In still another embodiment, the reference is a human subject or a population of subjects who had GBM, following surgical removal of a GBM tumor. In another embodiment, the reference is a human subject or a population of subjects who had GBM and was evaluated for target isoform levels prior to surgical removal of a GBM tumor. Similarly, in another embodiment, the reference is a human subject or a population of subjects evaluated for target isoform levels following therapeutic treatment for GBM. In still another embodiment, the reference is a human subject or a population of subjects prior to therapeutic treatment for an GBM. In still other embodiments of methods described herein, the reference is obtained from the same test subject who provided a temporally earlier biological sample. That sample can be pre- or post-therapy or pre- or post-surgery.

Other potential reference standards are obtained from a reference that is a human subject or a population of subjects having early stage or late stage GBM or one of the four identified subtypes. In another embodiment, the reference standard is a combination of two or more of the above reference standards.

Selection of the particular class of reference standards, reference population, target isoform levels or profiles depends upon the use to which the diagnostic/monitoring methods and compositions are to be put by the physician and the desired result, e.g., initial diagnosis of GBM, subtype identification, or other GBM condition, clinical management of patients with GBM after initial diagnosis, including, but not limited to, monitoring for reoccurrence of disease or monitoring remission or progression of the cancer and either before, during or after therapeutic or surgical intervention, selecting among therapeutic protocols for individual patients, monitoring for development of toxicity or other complications of therapy, predicting development of therapeutic resistance, and the like. Such reference standards or controls are the types that are commonly used in similar diagnostic assays for other target isoforms.

"Sample" as used herein means any biological fluid or tissue that contains the GBM cancer target isoforms identified herein. In one embodiment, the sample is GBM tumor tissue or biopsy. In one embodiment, the sample is cerebrospinal fluid or a tumor secretome. Other samples for use in the methods and with the compositions are samples which require minimal invasion for testing include, e.g., blood samples, including serum, plasma, whole blood, and circulating tumor cells, cerebrospinal fluid, ascites fluid, tumor secretome fluid, peritoneal fluid, and RNA isolated therefrom.

It is also anticipated that other biological fluids, such as saliva or urine, and ascites fluids or peritoneal fluid may be similarly evaluated by the methods described herein. Also, circulating tumor cells or fluids containing them are also suitable samples for evaluation in certain embodiments of this invention. Such samples may further be diluted with saline, buffer or a physiologically acceptable diluent. Alternatively, such samples are concentrated by conventional means. The samples may be prepared for analysis by the methods described herein by isolation of RNA from the sample.

The term "ligand" refers with regard target isoforms to a molecule that binds or complexes, or hybridizes with an isoform nucleotide sequence, e.g., polynucleotide or oligonucleotide, primers or probes. Only if a protein assay is employed as discussed above, would the ligand be of the type that would bind or complex to a protein expression product of the isoform, if any existed.

As used herein, "labels" or "reporter molecules" are chemical or biochemical moieties useful for labeling a ligand. "Labels" and "reporter molecules" include fluorescent agents, chemiluminescent agents, chromogenic agents, quenching agents, radionucleotides, enzymes, substrates, cofactors, inhibitors, radioactive isotopes, magnetic particles, and other moieties known in the art. "Labels" or "reporter molecules" are capable of generating a measurable signal and may be covalently or noncovalently joined to a ligand.

It should be understood that while various embodiments in the specification are presented using "comprising" language, under various circumstances, a related embodiment is also be described using "consisting of" or "consisting essentially of" as language. It is to be noted that the term "a" or "an", refers to one or more, for example, "a gene transcript," is understood to represent one or more gene transcripts. As such, the terms "a" (or "an"), "one or more," and "at least one" is used interchangeably herein.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

II. DIAGNOSTIC REAGENTS, DEVICES AND KITS

In one aspect, an isoform-level gene panel is provided that can accurately classify a glioblastoma subtype as Proneural (PN), Neural (N), Mesenchymal (M) or Classical (C) from a tumor sample comprises a group of target isoforms selected from those identified in Table 1. As disclosed in the examples below, use of the methods and assays described herein with these new isoform-level signatures permits refining of the four known subtype classifications. The refinement involves re-assigning some patient samples to a different sub-group (see Table 4), leading to a better prognostic stratification (see FIG. 2C). In one embodiment, the isoform gene panel contains the 121 isoform targets of Table 1. In another embodiment, the isoform gene panel contains all 214 isoform targets of Table 1. These isoform panels may be immobilized on a substrate, wherein the substrate is a microarray, a microfluidics card, a chip, a bead, or a chamber.

In another aspect, a kit, panel or microarray is provided comprising multiple ligands, each ligand capable of specifically complexing with, binding to, hybridizing to, or quantitatively detecting or identifying a single target isoform. In one embodiment, the total number of isoform targets, and thus ligands, in a kit are selected from the 121 target isoforms of Table 1, the 214 target isoforms of Table 1, or some combination thereof. In another embodiment, a kit, panel or microarray can include suitable labeled or immobilized ligands in a number of at least 50, 100, 121, 150, 200 or 214 of the isoform targets of Table 1. In still another embodiment at least one ligand of the kit, panel or microarray is associated with a detectable label or with a substrate. In another embodiment, each ligand identifies the level of expression or activity of a different target isoform of Table 1. In still further embodiment, the kit, panel or microarray described herein comprises ligands that individually bind to or complex or hybridize and identify the level of expression or activity of all 121 target isoforms identified in the top of Table 1 or all 214 isoform targets including those identified at the lower portion of Table 1.

Still additional kits, panels or microarrays described herein contain other ligands or reagents that identify the level of expression or activity of the controls that are upregulated in GBM relative to a normal reference standard. In another embodiment, the kit, panel or microarray comprises ligands or reagents that identify the level of expression or activity of the controls that are downregulated in GBM relative to a normal reference standard. In still a further embodiment, the kit, panel or microarray comprises ligands or reagents that identify the level of expression or activity of endogenous controls or housekeeping genes, such as those identified in Table 1.

As discussed above, the kit, panel or microarray is designed, wherein each ligand is selected from a nucleotide or oligonucleotide sequence that binds to or complexes or hybridizes with a single isoform target of Table 1. For example, such ligand directed to a single isoform target is a PCR oligonucleotide primer or probe, or a pair of PCR oligonucleotide primers or probes. Such sequences bind to or complex or hybridize with a single isoform target of Table 1. Such a polynucleotide/oligonucleotide probe or primer may itself be labeled or immobilized. In one embodiment, ligand-hybridizing polynucleotide or oligonucleotide reagent(s) are part of a primer-probe set, and the kit comprises both primer and probe. Each the primer-probe set amplifies a different target isoform of Table 1, optionally including the control isoforms and housekeeping genes.

For use in the compositions the PCR primers and probes are preferably designed based upon the isoform sequences present in Table 1. The design of the primer and probe sequences is within the skill of the art based on selection of each isoform target. The particular methods selected for the primer and probe design and the particular primer and probe sequences are not limiting features of these compositions. A ready explanation of primer and probe design techniques available to those of skill in the art is summarized in U.S. Pat. No. 7,081,340, with reference to publically available tools such as DNA BLAST software, the REPEAT MASKER program (Baylor College of Medicine), Primer Express (Applied Biosystems); MGB assay-by-design (Applied Biosystems); Primer3 (Steve Rozen and Helen J. Skaletsky (2000) Primer3 on the WWW for general users and for biologist programmers and other publications.

In general, optimal PCR primers and probes used in the compositions described herein are generally 17-30 bases in length, and contain about 20-80%, such as, for example, about 50-60% G+C bases. Melting temperatures of between 50 and 80° C., e.g. about 50 to 70° C. are typically preferred.

The kits, panels or microarrays may further include labels selected from among many known diagnostic labels, including those described above. Similarly, the substrates for immobilization of one or more, or all of the isoform targets or may be any of the common substrates, glass, plastic, a microarray, a microfluidics card, a chip, a bead or a chamber. In another embodiment, the kit also contains optional substrates for enzymatic labels, as well as other laboratory items.

Still further components of the kit, panel or microarray as described herein can include other known reagents and components for conducting an RNA-based assay, including RNA-seq or mRNA-seq assay by NextGen sequencing of RNA, or a customized microarray panel consisting of e.g., the 214 total transcripts or 121 "signature" transcripts of Table 1, or some combination thereof, plus controls, presented on e.g., AFFYMETRIX exon-array; AGILENT microarray; ILLUMINE microarray, also a NONOSTRING assay, ILLUMINA HISEQ assay. In the exemplified embodiment of the examples, an RT-qPCR based assay was employed to identify and/or measure the levels of these isoform or gene transcripts in a sample.

Any combination of labeled or immobilized target isoform ligands can be assembled in a diagnostic kit or device for the purposes of diagnosing brain cancer, brain tumor or a glioblastoma or subtype thereof.

As still a further embodiment, the kit, panel or microarray further comprising computer software that performs the functions outline in FIG. 8 and as discussed below.

The selection of the ligands, groups of target isoforms and sequences, their length, suitable labels and substrates used in the reagents and kits are routine determinations made by one of skill in the art in view of the teachings herein of which target isoforms form signatures suitable for the diagnosis of brain cancer, brain tumor or a glioblastoma.

Figure 7:
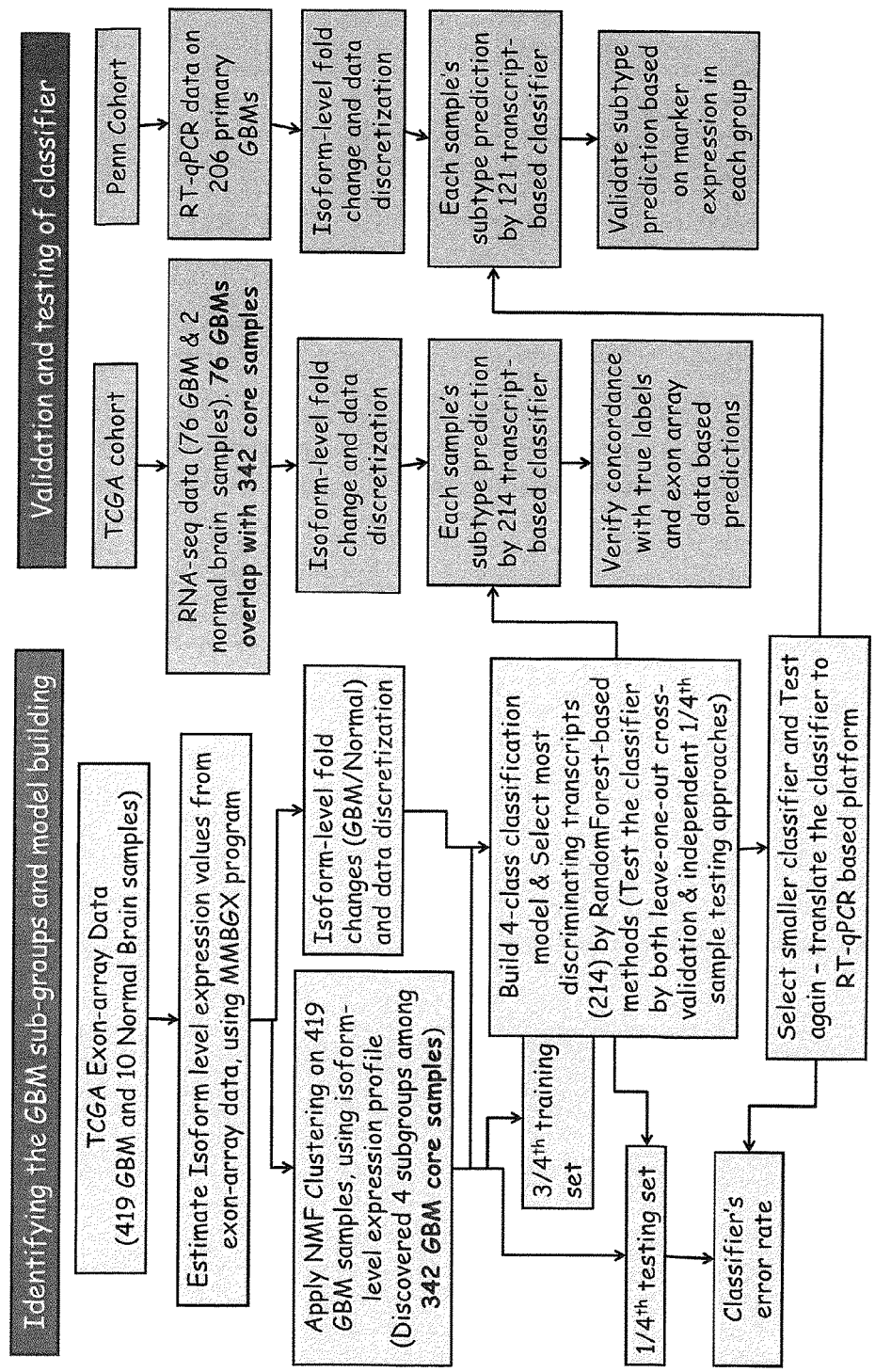
FIG. 7 is a flow-chart illustrating the process of identifying the GBM sub-groups and building the model for selecting and generating the classifier and transitioning to RT-PCR and RNA-sequence platforms. Also shown in the process for validating and testing of the classifier

The selection and validation of the target isoforms for use in these diagnostic reagents and kits are summarized in detail in FIG. 7.

III. METHODS FOR DIAGNOSING OR MONITORING BRAIN CANCER, BRAIN TUMOR OR A GLIOBLASTOMA OR SUBTYPE THEREOF

In another embodiment, a method for diagnosing or detecting, predicting the subtype, or monitoring the progress of brain cancer, brain tumor or a glioblastoma in a subject comprises, or consists of, a variety of steps. These steps are also summarized with the necessary algorithms in FIG. 8. This method may employ any of the suitable diagnostic reagents or kits or compositions described above.

The test sample is obtained from a human subject who is to undergo the testing or treatment. The subject's sample can in one embodiment be provided before initial diagnosis, so that the method is performed to diagnose the existence of a brain cancer, brain tumor or a glioblastoma. In another embodiment, depending upon the reference standard and target isoforms used, the method is performed to diagnose the subtype or brain cancer, brain tumor or a glioblastoma. In another embodiment, depending upon the reference standard and markers used, the method is performed to diagnose the stage of brain cancer, brain tumor or a glioblastoma. In another embodiment, the subject's sample can be provided after a diagnosis, so that the method is performed to monitor progression of n brain cancer, brain tumor or a glioblastoma. In another embodiment, the sample can be provided prior to surgical removal of a tumor or prior to therapeutic treatment of a diagnosed brain cancer, brain tumor or a glioblastoma and the method used to thereafter monitor the effect of the treatment or surgery, and to check for relapse. In another embodiment, the sample can be provided following surgical removal of a tumor or following therapeutic treatment of a diagnosed brain cancer, brain tumor or a glioblastoma, and the method performed to ascertain efficacy of treatment or relapse. In yet another embodiment the sample may be obtained from the subject periodically during therapeutic treatment for a brain cancer, brain tumor or a glioblastoma, and the method employed to track efficacy of therapy or relapse. In yet another embodiment the sample may be obtained from the subject periodically during therapeutic treatment to enable the physician to change therapies or adjust dosages. In one or more of these embodiments, the subject's own prior sample can be employed in the method as the reference standard.

Where the sample is a fluid, e.g., cerebrospinal fluid, blood, serum or plasma, obtaining the sample involves simply withdrawing and preparing the sample for isolation of RNA therefrom in the traditional fashion for use in the methods. Where the sample is a tissue or tumor or biopsy sample, it may be prepared as described in the examples below for isolation of RNA therefrom, or any conventional manner prior to performance of the assay.

The isoform-level assay for diagnosis of brain cancer, e.g., for prediction or diagnosis of the molecular subtype of a glioblastoma multiforme, in a subject thus comprises the following steps. One embodiment of the method, as well as the function of the computer program and its algorithms is outlined in FIG. 8.

The biological sample obtained from a subject that has or is suspected of having a glioblastoma is contacted with an isoform panel having target isoforms selected from Table 1, or a combination thereof, or a reagent, kit, panel or microarray of ligands capable of specifically complexing with, binding to, or quantitatively detecting or identifying the level or activity of target isoforms of Table 1 or a combination thereof. In one embodiment, such contact occurs in the performance of an RNA-based assay, such as RT-qPCR assay or an ILLUMINA HISEQ assay.

Other commonly used methods known in the art for the quantification of mRNA expression in a sample include northern blotting and in situ hybridization; RNAse protection assays; and PCR-based methods, such as reverse transcription polymerase chain reaction (RT-PCR) or qPCR. The methods described herein are not limited by the particular techniques selected to perform them. Exemplary commercial products for generation of reagents or performance of assays include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test), the MassARRAY-based method (Sequenom, Inc., San Diego, Calif.), differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) and high coverage expression profiling (HiCEP) analysis.

As described in the examples below and summarized in FIG. 8, the PCR assays involves contact of the sample with 121 isoform transcripts of Table 1, 15 control transcripts and 4 housekeeping genes. The individual levels or activities of the target isoforms relative to a reference standard, e.g., normal population with no cancer, are then determined in the RNA sequence based protocol. Thereafter the results of the RNA based assay are analyzed in a computer program performing the functions as described in FIG. 8. The program generates an isoform signature that permits a diagnosis or prediction of the subject's GBM molecular subtype.

The PCR cycle value of each isoform target transcript is obtained and manipulated by the algorithm $Ct_{transcript\ 1} - Ct_{Polr2A} = DelCt_{GBM}$ (which is the DelCt of the patient sample). Then the $\log_2$ Foldchange between the patient's value and normal is calculated using $DelCt_{normal}$, which was the DelCt values for normal brain obtained using 136 transcripts/genes as described in more detail in the examples. DelCt is used in calculation of fold change based on qPCR output which is Ct value when we perform relative quantification. DelCt is defined as the difference between the Ct value of a given transcript/isoform (one of the 214/121 transcripts or control 15 transcripts) and the Ct value of the normalization control gene, which in our case is Polr2a in the same samples. This value is then added to the PCR data matrix which was generated for 206 GBM patients as described in the examples below. The fold change is then discretized with 20 bins and the classifier, e.g., the 121 signature target isoform transcripts based panel or the 215 target isoform transcript panel, is applied on the discretized data.

Thereafter the predicted subtype of the sample based on maxP is obtained. This protocol is defined more specifically in the examples below.

In one embodiment, the assay includes in the PCR step, the ligands directed to the controls identified in Table 1. In another embodiment, the ligands are those capable of specifically complexing with, binding to, or quantitatively detecting or identifying the level or activity of all 121 signature target isoforms identified in the top portion of Table 1 and the controls identified in Table 1. In another embodiment, the ligands used in the PCR are those directed to all 214 isoform targets of Table 1. In still another embodiment, the ligands used in the method are a combination of those generated to isoform targets selected from the 214 isoform targets of Table 1.

For the performance of the PCR portion of the method, the reference standard is a mean, an average, a numerical mean or range of numerical means, a numerical pattern, a ratio, a graphical pattern or a protein level profile derived from the same isoforms in a reference subject or reference population. For example, the reference standard is selected from a reference subject or reference population selected from the group consisting a reference human subject or a population of healthy with no glioblastoma multiforme (GBM); a reference human subject or a population of subjects having benign nodules; a reference human subject or a population of subjects following surgical removal of a GBM tumor; a reference human subject or a population of subjects prior to surgical removal of a GBM tumor; a reference human subject or a population of subjects following therapeutic treatment for a GBM tumor; a reference human subject or a population of subjects prior to therapeutic treatment for a GBM tumor; or the same subject who provided a temporally earlier biological sample.

In addition to making an initial clinical diagnosis of GBM or subtype of GBM, this method can be used to monitor relapse after initial diagnosis and treatment, predict clinical outcome or determine the best clinical treatment.

In yet another aspect, a modified method and algorithm for identifying classes of isoform level gene expression that are useful for identifying diseases or conditions is the Platform-independent Isoform-level Gene expression based classification system (PIGExClass).

The basic steps in PIGExClass algorithm are described below:

To derive numerically comparable measures of gene expression between different platforms, and translate the gene-panel (from the classifier) across platforms, we developed PIGExClass by combining a novel data-discretization[1] procedure with "variable selection" step, a randomForest-based variable selection algorithm[2]. The PIGExClass algorithm is available as a set of R scripts and reproduced in FIGS. 16A and 16B.

Step 1: Data-Discretization Step (Normalization Procedure for Cross Platform Transformation of Fold-Change Data):

We applied data discretization for converting continuous data values into categorical data (1). Basically, we discretized the fold-change levels (GBM over normal brain) of each transcript expression from each platform based on equal frequency or equal width binning (1) and converted the continuous fold change data to categorical values (FC-CVs—Fold Change Categorical Values), using the following procedure.

1. For each transcript/gene, sort the samples based on fold changes (FCs) in ascending order.

2. Divide sorted vector into a predetermined number of bins, so that the width of all bins is equal (equal-width binning) or the number of samples in each bin is equal (equal-frequency binning). The number of categories (bins) was determined whether finer or coarser discretization improves the accuracy of the classification model. Similarly, the choice between equal-frequency binning or equal-width binning was made depending on the accuracy of the derived classification model.

3. Each fold change value is replaced by an integer value corresponding to the rank of the bin it falls into.

Step 2: Variable Selection and Classification Steps:

Prior to building the classification model, we applied a randomForest-based variable selection algorithm (2) to select a small set of non-redundant genes or isoforms, using FCCVs. The variable selection was performed separately on gene-level or transcript-level fold changes. By selecting 213 transcripts/isoforms as the most discriminative variables between the four GBM subgroups, we created a randomForest classifier for subtype prediction (3,4). The cross-validation analysis of the final selected classifier was done by out-of-bag [OOB] approach. We further tested the classifier by dividing the isoform-based core samples into $3/4^{th}$ as training-set and $1/4^{th}$ as test-set. The classification model generated from the training set was applied to the test set.

RNA-seq data analysis: The TCGA GBM paired-end RNA-seq aligned barn files, for a total of 155 patient samples, were downloaded. A subset (76 datasets) of GBM samples have expression profiles from both RNA-seq and exon-array platforms. The RNA-seq barn files were converted to raw fastq files by Picard tools. The isoform level expression estimates were obtained by Tophat/Cufflinks pipeline using Ensembl 66 as reference (5) and expression estimates were normalized by upper quartile normalization. Two normal brain RNA-seq samples (used as controls to calculate expression fold-changes and FCCVs GBM over normal brain) were downloaded from SRA archive (ERR030882 and SRR309262) and analyzed using the same pipeline as the GBM samples.

Evaluation of the data-mining algorithm on RNA-seq data: We evaluated the transition of the PIGExClass from exon-array to an independent platform by applying the classifier (trained on exon-array data) on GBM RNA-seq samples. Misclassification rate was computed based on 76 GBM samples overlapped with the isoform-level core samples and profiled by both exon-array and RNA-seq methods. We have calculated the Pearson correlation between each pair of expression signatures (fold changes), before and after data discretization, for the 76 GBM samples that were profiled by both exon-array and RNA-seq platforms.

GBM Tissue Specimens: The GBM samples processed for RNA isolation were obtained from the Human Brain Tumor Tissue bank (HBTTB) at The University of Pennsylvania. Collection of brain tumor tissue was approved by the Hospital of the University of Pennsylvania Institutional Review Board, with wavier of informed consent for retrospective review of medical records. Procurement and processing of GBM tumor tissues from HBTTB was approved by the Wistar Institute's Institutional Review Board.

Open array design: To measure the expression of transcripts selected in the classifier we designed RT-qPCR assays to be performed on the high throughput OpenArray platform (Life Technologies Inc.). In one embodiment, the RandomForest algorithm discovered sets of isoforms that are discriminative between the 4 sub-groups of GBMs, as discussed in the examples below.

RNA isolation and RT-qPCR analysis: RNA was isolated using Tri Reagent (Sigma Inc.) and cDNA was synthesized using the high capacity cDNA reverse transcriptase kit (Applied Biosystems Inc.) according to manufacturer's instructions. Normal brain RNA was purchased from Agilent Inc.

Figure 8:
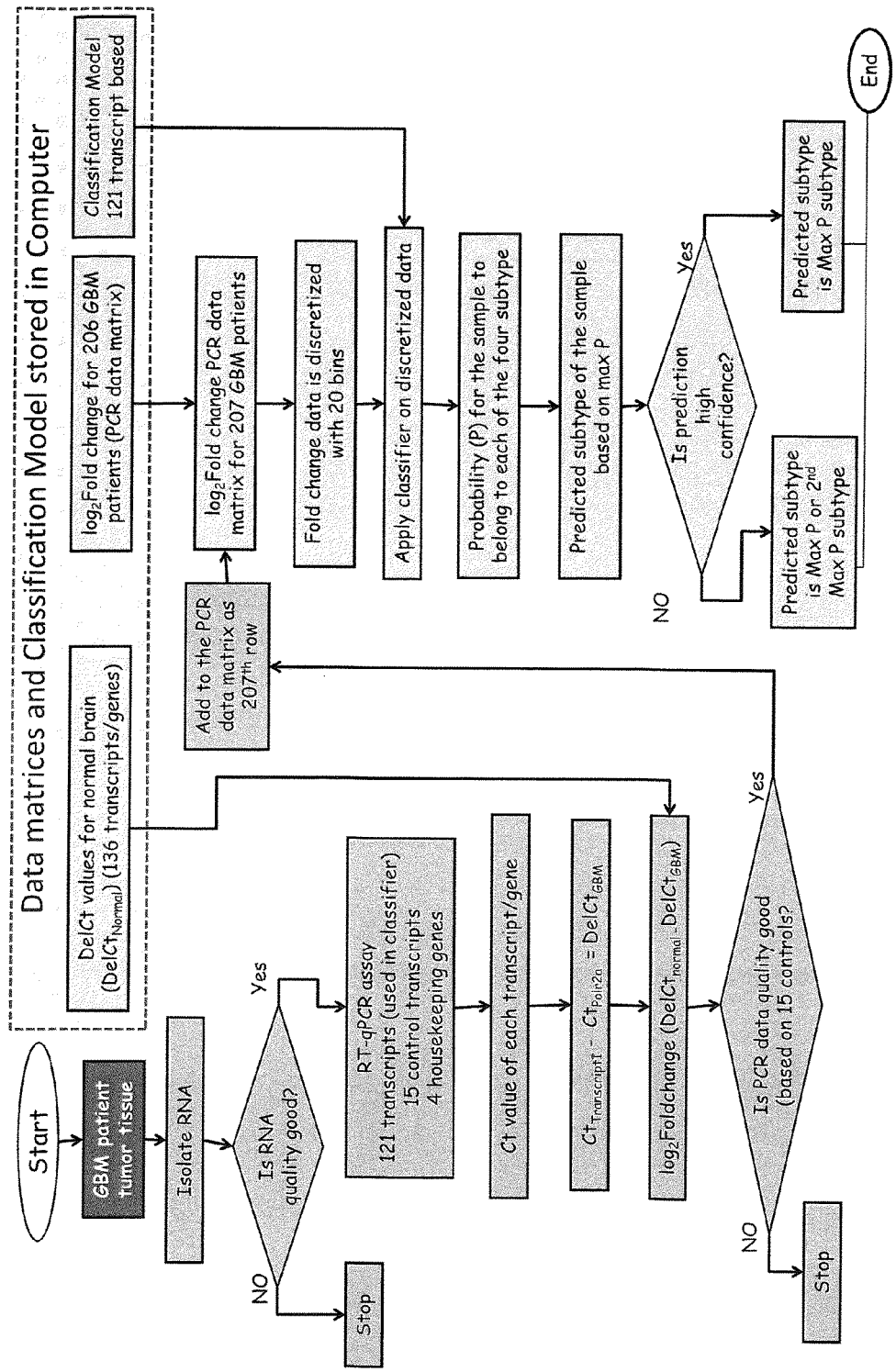
FIG. 8 is the flow chart illustrating the performance of the computer program that analyzes the data from the diagnostic assay using the 121 isoform assay described herein. Abbreviations used in the flow charts include: Polr2A, which is a gene used as a control on PCR assays; Ct, which is the cycle number obtained for a gene/transcript in a PCR assay; DelCt refers to Delta Ct value, a standard PCR measure. The PCR data-matrix is the data of 206 rows and 121 columns. Rows represent patients and columns represent Transcript IDs. Each entry in this matrix is a fold-change value (ratio of expression of a transcript in a patient sample over the expression of that transcript in normal brain) for the Xth transcript and Yth patient. The classifier is a RandomForest built model built from the original data matrix of the 342 TCGA GBM samples used in the process depicted in FIG. 7.
Figure 9:
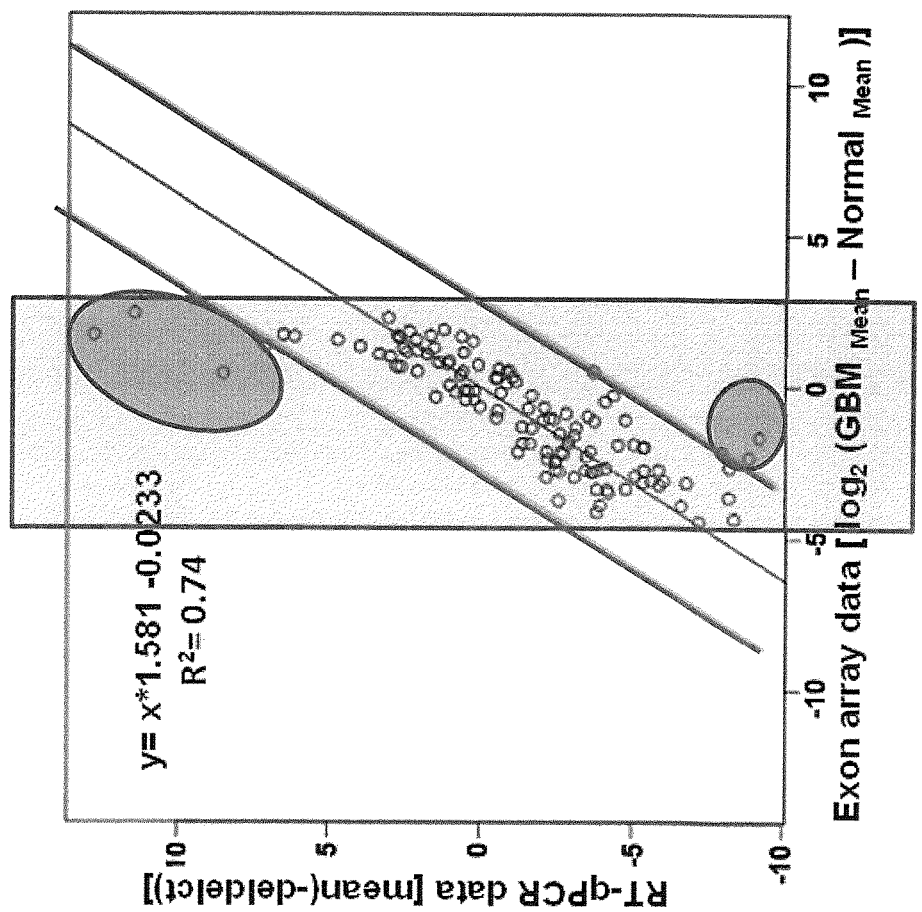
FIG. 9 is a graph showing Exon-array and RT-PCR correlations using the 121 isoform transcript classifier. Rt PCR data was linear transformed based on the equation in the graph.
Figure 10:
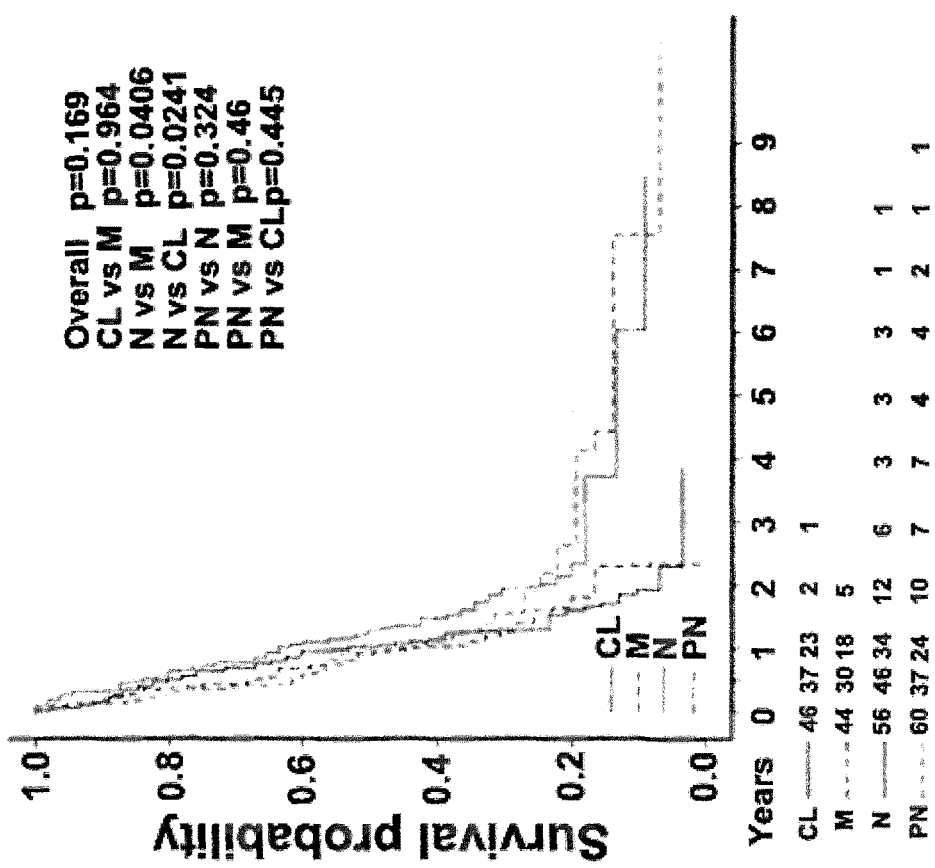
FIG. 10 is a graph showing survival curve for the four subtypes of GBM patients (Penn GBM cohort).

The method described herein can be performed at least partially by use of a properly programmed a computer processor or computer-programmed instrument that generates numerical or graphical data useful in the diagnosis of the condition using the functions and algorithms identified in FIG. 8.

In another aspect of the method, a computer program or source code that performs the functions and uses the algorithms of the flow chart of FIG. 8 is provided. It is anticipated that based on this disclosure, one of skill in the art may also generate similar or slightly modified programs that use the above-described diagnostic reagents and isoform transcript panels of Table 1 in a similar manner.

The results of the methods and use of the compositions described herein may be used in conjunction with clinical risk factors to help physicians make more accurate decisions about how to manage patients with brain cancer, brain tumor or a glioblastomas.

Thus, the various methods, devices and steps described above can be utilized in an initial diagnosis of brain cancer, brain tumor or a glioblastoma or other condition, as well as in clinical management of patients with brain cancer, brain tumor or a glioblastoma after initial diagnosis. Uses in clinical management of the various devices, reagents and assay methods, include without limitation, monitoring for reoccurrence of disease or monitoring remission or progression of the cancer and either before, during or after therapeutic or surgical intervention, selecting among therapeutic protocols for individual patients, monitoring for development of toxicity or other complications of therapy, and predicting development of therapeutic resistance.

As described and supported by the examples below, one major advantage of isoform-based subtyping of the TCGA primary GBM samples was in survival stratification. Unlike previous studies,[3,4,33] we found significantly better survival for the PN subgroup in the TCGA GBM cohort. Interestingly, we also observed that this survival advantage for the PN subgroup was relevant only for younger patients. Although isoform-based core samples of the TCGA cohort is much larger (342 samples) than the core group analyzed by the TCGA network,[3] this difference in the PN prognostic value between isoform- and gene-based classification is not due to unequal representation of younger patients in both studies (~16% patients <40 years in both studies). However, we did not observe a better survival rate for the PN group in the Penn cohort due to underrepresentation of younger patients. Strikingly, we observed better survival for the neural subtype, and most of the older patients who survive beyond three years belong to the PN or N subtypes in the Penn cohort. In comparison, the older and longer-surviving patients in the TCGA cohort were spread across the four subtypes, suggesting differences in the responses to surgery and chemotherapy/radiation therapies across the various tissue collection centers.

The prevalence of various mutations among the patients of the four subgroups defined by isoform-based clustering was analyzed (see Table 2 below). Though certain mutations tend to be associated with specific subtypes, only a fraction of primary GBM patients within each group harbor these mutations, indicating that mutational analysis is not an effective tool for accurately classifying GBM patients.

TABLE 2

Distribution of Frequently Mutated Genes across GBM Subtypes

| Gene | Proneural n = 31 | | Neural n = 36 | | Mesenchymal n = 34 | | Classical n = 17 | | Total # GBMs with Mutations | | |
|---|---|---|---|---|---|---|---|---|---|---|---|
| | ≤40Y 17 | >40Y 14 | ≤40Y 3 | >40Y 33 | ≤40Y 2 | >40Y 32 | ≤40Y 1 | >40Y 16 | ≤40Y 23 | >40Y 95 | Total 118 |
| TP53 | 8 20% | 6 15% | 2 5% | 8 15% | 2 5% | 12 30% | 1 3% | 1 3% | 13 | 27 | 40 |
| NF1 | 2 11% | 0 | 0 | 7 37% | 1 5% | 8 37% | 0 | 1 5% | 3 | 16 | 19 |
| EGFR | 2 11% | 1 5% | 1 5% | 9 47% | 0 | 1 5% | 1 5% | 4 21% | 4 | 15 | 19 |
| IDH1 | 6 60% | 2 20% | 2 20% | 0 | 0 | 0 | 0 | 0 | 8 | 2 | 10 |
| PIK3R1 | 5 50% | 1 10% | 0 | 3 30% | 0 | 0 | 0 | 1 10% | 5 | 5 | 10 |
| DST | 3 50% | 0 | 0 | 0 | 0 | 0 | 0 | 3 50% | 3 | 3 | 6 |
| ANK2 | 0 | 0 | 0 | 0 | 0 | 3 100% | 0 | 0 | 0 | 3 | 3 |
| CHEK1 | 0 | 0 | 0 | 0 | 0 | 0 | 0 | 2 100% | 0 | 2 | 2 |
| HSPA8 | 0 | 0 | 0 | 0 | 0 | 0 | 0 | 2 100% | 0 | 2 | 2 |

In agreement with the previous reports, NF1 mutations were found mostly in the M and N subtypes and EGFR mutations, including EGFRvIII, mostly in the CL and N subtypes. While only 8% of the TCGA GBM patients had an IDH1 mutation, 60% of the IDH1-mutated patients were of the PN subtype and younger than 40 years.

Interestingly, five out of six patients with the IDH1 mutation were from the MD Anderson center. The IDH1 mutation is a hallmark for low-grade gliomas and secondary GBMs that arise from low-grade gliomas.[38] Histologically, primary and secondary GBMs are similar in appearance,[29] and it is possible that GBMs with the IDH1 mutation, especially younger patients who have been clinically diagnosed with primary GBMs, could be, in fact, secondary GBMs that progressed from low-grade gliomas that escaped clinical diagnosis at early low-grade status.[39] This could be one possible explanation for the higher representation of young PN subtype patients in the TCGA GBM cohort who came mostly from the MD Anderson center. This speculation is further supported by the fact that secondary GBMs were classified as PN subtype in the TCGA network study.[3]

The compositions and methods described herein can be applied in ongoing clinical trials to determine recruited patients' subtypes for evaluating the subtype-specific efficacy of the drugs being tested.[46] The inventors discovered 2.6 times more changes at isoform-level than at the gene-level in the glioblastoma transcriptome. Using isoform-level expression clustering, four GBM subgroups were identified with significant (p=0.0103) survival differences. A four-class classifier, built with 121 transcript-variants, assigns GBM patients' molecular subtype with 92% accuracy. The GBM classifier was translated to an RT-qPCR-based assay and validated on an independent cohort of 206 glioblastoma samples, and maintained high-confidence subtype calls for 91% of the patients. We found the proneural subtype to have the worst prognosis for patients, except for the younger group (<40 years) who showed significantly better survival (p=0.007), while a better prognosis for the neural subtype was observed (p=0.02) in older patients (≥40 years). An isoform-level expression signature produced an accurate quantitative molecular diagnostic assay with improved prognostic stratification of GBM patients.

We considered that the isoform-level expression profiling generates better classification to identify the molecular sub-groups of GBM. To test this hypothesis, we performed isoform-level analysis of the exon array expression data for GBM patient samples from the TCGA data portal, and discovered that isoform-level analysis identifies 2.5 fold more differentially expressed transcript variants than differentially expressed genes captured by gene-level analysis, indicating that isoform-level expression profiling is more sensitive in identifying molecular changes among GBM patients. Next, we applied consensus non-negative matrix factorization (NMF) clustering method, based on isoform-level expression of most variable isoforms and effectively grouped the GBM samples into 4 sub-groups with significant (p=0.0103) survival differences between the groups. In contrast, though clustering based on gene-level expression produced four homogenous groups there was no significant survival difference among the sub-groups. Based on the prognostic value of the molecular sub-groups, the goal was to build a classifier that can assign each GBM patient a molecular sub-group. We compared the prediction accuracy of a gene based vs an isoform based classifier to identify sub-group and found that isoform based classifier is a better predictor (85% vs 90%). Using the Random forest feature selection we have built a classifier based on the expression of 121 isoforms that is ~91% accurate and have developed a high throughput RT-qPCR assay to measure the expression of these discriminatory isoforms. We have successfully validated the classifier to identify the molecular sub-group in an independent cohort of GBM patient samples from the Human Brain Tumor Tissue bank at University of Pennsylvania. the study has led to the development of a classification assay for GBM patient sub-grouping and suggests that isoform based expression analysis can lead to better molecular classification of cancer, a requirement for the quest of personalized therapy.

V. EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1: Materials and Methods

Recent genome-wide studies have discovered that the majority of human genes produce multiple transcript-variants and protein isoforms, which could be involved in different functional pathways.[6] Moreover, altered expression of transcript-variants and protein isoforms for numerous genes is linked with cancer and its prognosis, as cancer cells manipulate regulatory mechanisms to express specific isoforms that confer drug resistance and survival advantages.[7] For example, cancer-associated alterations in alternative exons and splicing machinery have been identified in cancer samples,[8-13] demonstrating the efficacy of specific transcript-variants as diagnostic and prognostic markers.[14]

Statistical analysis was performed on The Cancer Genome Atlas (TCGA) datasets to determine differentially expressed genes and isoforms between GBM and normal brain. Machine-learning approaches were applied to derive robust stratification of GBM samples, select the most discriminatory transcript-variants and build an accurate classifier. A high-throughput RT-qPCR assay was designed to quantify the expression of selected transcript-variants and to validate the classifier in an independent GBM cohort. The entire process is depicted in the flow chart of FIG. 7.

The OpenArray platform with 168-plate format was used for RT-qPCR assays to measure the expression of transcripts selected in the classifier. The GBM samples for validating the classifier were obtained from the Human Brain Tumor Tissue bank at The University of Pennsylvania. Collection of brain tumor tissue was approved by the Hospital of the University of Pennsylvania Institutional Review Board, with wavier of informed consent for retrospective review of medical records. Procurement and processing of GBM tumor tissues from HBTTB was approved by the Wistar Institute's Institutional Review Board.

(a) Statistical Analysis:

The expression estimates from the exon-array data were obtained by the Multi-Mapping Bayesian Gene eXpression algorithm for Affymetrix whole-transcript arrays[15] based on Ensembl database (version 56). The estimated expression levels were normalized using the locally weighted scatter-plot smoothing (loess) algorithm.[16] Differentially expressed genes and isoforms between GBM and normal brain samples were determined using the limma method.[17] NMF clustering method[18,19] was applied to cluster the TCGA samples by using the expression of 1,600, non-redundant isoforms with the highest variability across the samples. Kaplan-Meier survival curves among the four GBM isoform expression subtypes are plotted. Log-rank test was applied to test if there were a difference between the survival curves. Random Forest-based classification and feature-variable selection algorithms[20,21] were applied to build the classifier for subtype prediction.

(b) Preprocessing of TCGA Exon-Array Data:

We downloaded the unprocessed Affymetrix Exon-array datasets for 426 GBM samples and 10 normal brain samples (control samples) from the TCGA data portal. We removed 7 GBM samples for which no survival information was available. We, therefore, analyzed raw exon-array data of 419 GBM and 10 normal brain samples. The transcript (isoform)-level and gene-level expression estimates were obtained by the Multi-Mapping Bayesian Gene eXpression (MMBGX) algorithm[15] for Affymetrix whole-transcript arrays, based on Ensemble database (version 56), which contains a total of 114,930 different transcript annotations that correspond to 35,612 different gene models. This method takes into account the multi-mapping structure between probes of the exon-array and the features the probes target. The MMBGX algorithm was published as an R package. The estimated expression values were then normalized across the samples, using the locally weighted scatter plot smoothing (loess) algorithm[16].

After obtaining the isoform-level gene expression estimates and data normalization, the subgroup discovery from TCGA GBM samples was performed by following data-filtering and clustering methods that were applied in previous TCGA publications.[3]

(C) Data Filtering (Selection of Most Variable Isoforms/Transcript Variants for Sample Clustering):

Two filters were applied here. The first filter was applied to retain only one isoform among highly correlated isoforms of same gene. Two isoforms of a gene are considered highly correlated if the Pearson's correlation coefficient of isoform-level expressions across the samples is higher than 0.8. The isoform with highest coefficient of variation (CV), highest variability across patients, was retained among the correlated isoforms of a gene. The second filter was applied to eliminate low-variable isoforms across the patients. We selected 1,600 isoforms with the highest variability across patients, using CV (coefficient of variation). Unlike standard deviation, which is heavily affected by the mean value of the data set, CV is a dimensionless number and a way to penalize the expressions with overall high expression values.

(d) Identification of GBM Subgroups Based on Isoform-Level Expression Using Consensus Non-Negative Matrix Factorization (NMF) Clustering:

We applied consensus NMF clustering approach to group the samples. This approach has been shown to be less sensitive to a priori selection of genes or initial conditions and having a better performance than hierarchical clustering and self-organizing maps[18]. NMF analysis was performed on expression matrix of 1600 transcripts and 419 samples using R package "NMF"[19]. To obtain non-negative matrices we used log transformed values to which the absolute value of the lowest log value has been added. For rank k=2-7, consensus matrices were obtained by taking the average of over 50 connectivity matrices. The stability of the decompositions was evaluated using a cophenetic correlation coefficient and visualization (FIG. 6) of a heat map plot of the consensus clustering matrix (heat map shown in FIG. 6A of parent application). As the NMF finds different solutions for different initial conditions, the factorizations were repeated 100 times using the previously determined rank and evaluated according to their factorization approximation error. The factorization with the lowest approximation error was retained.

The silhouette width[22] was computed to filter out expression profiles that were included in a subclass, but that were not a robust representative of the subclass. Observations with a large silhouette width (almost 1) are very well clustered, a small value (around 0) means that the observation lies between two clusters, and observations with a negative values are probably placed in the wrong cluster.

(e) Survival Difference Between Subtypes:

Kaplan-Meier survival curves for the four GBM subtypes are plotted. Log-rank test is applied to test if there is a difference between the survival curves. The R package "survival" was used to do the analysis.[26]

(f) Isoform Based Signature Identification:

Differentially expressed marker isoforms were determined for each sub-type by comparing each sub-type with the other three sub-types using the limma method.[17] The functions implemented in the R package "siggenes" are used to perform SAM analysis to identify genes/isoforms that are differentially expressed in bi-classifications of one subtype vs. all the others and normal vs. tumor. We used the cutoff to be the q-value <0.001.

(g) Identification of an Isoform-Based Classifier for Predicting the GBM Sub-Types:

Diaz-Uriarte and De Andres[20] presented a new method for gene selection that uses randomForest. The main advantage of this method is that it returns very small set of genes that retain high predictive accuracy. The variable selection procedure is based on randomForest using both backward variable elimination and the importance spectrum. It has been shown that this method has comparable performance to other classification methods, including DLDA, KNN, and SVM, and that the new gene selection procedure yields very small sets of genes (often smaller than alternative methods) while preserving predictive accuracy. The algorithms are publicized in the R package of varSelRF. We ran the feature selection algorithm using 3000 trees in the forest during each step of backward elimination and the final randomForest classifier was built using the selected transcripts with 15,000 trees in the forest. All the other parameters are set to be the default values.

For better evaluating the performance of the classifier, we trained the random Forest models on ¾th of the dataset and tested on the remaining ¼th of the dataset. We reported the OOB (out of bag) error rate of the final classifier based on the ¾ training dataset and also the error rate based on the untouched testing data set.

(h) Data Discretization to Transform Continuous Data to Categorical Data:

To derive numerically comparable measures of gene expression between different platforms, we adopted an approach similar to the quantile discretization[41] to translate the classification model trained from exon-array to RT-qPCR assay. Basically, we discretized the data of each platform based on equal frequency binning[23] and converted the discretized data to ranks. Specifically, the fold change expression values of each transcript across all the samples in one platform were sorted in ascending order first. The resulting sorted vectors were then discretized into a predetermined number of bins "b". Every expression value was then replaced by an integer value corresponding to the rank of the bin it falls into. The number of bins "b" was dependent on the sample size and was determined as the closest integer value for sample number divided by a factor of 10. Based on this criterion the number of bins for Penn cohort (206 samples) was 20 and that for TCGA RNA-seq cohort (155 samples) was 15. The randomForest classifier was trained on the discretized data of TCGA isoform-based exon-array core samples for each bin size.

(i) RNA-Seq Data Analysis:

The TCGA GBM paired-end RNA-seq aligned bam files, for a total of 155 patient samples, were downloaded. A subset (76 datasets) of GBM samples have expression profiles from both RNA-seq and exon-array platforms. Two normal brain RNA-seq samples were downloaded from SRA archive (ERR030882 and SRR309262) and analyzed using the same pipeline as the GBM samples. The RNA-seq bam files were converted to raw fastq files by Picard tools. The isoform level expression estimates were obtained by Tophat/Cufflinks pipeline[42] using Ensembl 66 as reference. Cufflinks isoform level expression estimates are normalized by upper quartile normalization.

Similar quartile discretization procedure, described previously, was applied on the RNA-seq normalized data and the classifier trained on the exon-array platform data was applied on the RNA-seq samples for validating the classification model efficiency on data from an independent platform.

(j) Open Array Design:

To translate the classifier that was built based on exon array data to a clinically applicable platform, we decided to measure expression of the desired transcripts using RT-qPCR assay. We searched for commercially available TaqMan assays on Life Technology Inc. website and selected assays that would detect the transcript of choice and the co-detected transcripts were highly correlated in expression pattern. Care was taken to avoid assays that would co-detect transcripts showing negative correlation at expression with the desired transcript.

Out of the 214 transcripts selected by the classifier, we picked assays for 126 transcripts including HOTAIR, a gene differentially expressed between neural and proneural subtypes. We also included assays for four housekeeping genes—POLR2A, GAPDH, β2-microglobulin, and ACTINβ, a marker for classical subgroup—NES, and another marker for mesenchymal subgroup-CHI3L1, eight transcripts mostly upregulated and another seven transcripts mostly down-regulated in GBM patients relative to normal brain tissue. We decided to use the OpenArray platform with 168 plate format to perform these assays in a highthroughput manner. Of the 126 assays, five assays did not work well so we excluded these from the analysis and hence the classifier that was translated to an RT-qPCR assay is based on the expression of 121 target transcripts with four housekeeping genes as controls for normalization, and another 15 assays as controls for general behaviour of expression changes in GBM patient samples relative to normal brain tissue. These targets and controls are identified in Table 1.

(k) Performance of the Diagnostic Method

The diagnostic method is illustrated in the flow chart of FIG. 8.

i. RNA Isolation:

The GBM samples processed for RNA isolation were obtained from the Human Brain Tumor Tissue bank (HBTTB) at The University of Pennsylvania. Collection of brain tumor tissue was approved by the Hospital of the University of Pennsylvania Institutional Review Board, with wavier of informed consent for retrospective review of medical records. Procurement and processing of GBM tumor tissues from HBTTB was approved by the Wistar Institute's Institutional Review Board. The samples received were stored frozen in RNA later (Life Technologies Inc.).

Each sample was thawed on ice and RNA later was removed before transferring the tissue to Tri Reagent (Sigma Inc.). We used 1 ml of Tri reagent for approximately 50-75 mg of tissue, which was immediately homogenized using disposable homogenization tips (Omni International Inc.) and samples transferred to 1.5 ml eppendorf tubes. The homogenized samples were processed to isolate RNA as per manufacturer's instruction (Sigma Inc.). The concentration and purification of RNA was estimated by measuring absorbance at 260, 280, and 230 nm using the nanodrop instrument's nucleic acid-RNA program. RNA samples with poor 260/280 ratios (<1.8) were extracted with Tri reagent and samples with poor 260/230 ratio (<1.8) were re-precipitated with sodium acetate and ethanol overnight, washed with 70% ethanol and resuspended in DEPC treated water before concentration measurement and purification assessment. To check for RNA integrity all samples were analyzed on bioanalyzer using a RNA pico chip (Agilent technologies Inc.) and only samples with RIN≥5.0 were selected for RT-qPCR analysis. Normal brain RNA was purchased from Agilent Technologies Inc.

ii. RT-qPCR Analysis:

RNA samples with abs 260/280>1.8, 260/230>1.8, and RIN≥5.0 were selected for RT-qPCR analysis. For RT reaction, 2.5 µg of RNA was reverse transcribed using the high capacity cDNA reverse transcriptase kit (Applied Biosystems Inc.) according to the manufacturer's instruction. For the qPCR analysis, the cDNA (the RT reaction) was mixed with OpenArray real time RT-PCR master mix (Applied Biosystems Inc.) in the 384 well OpenArray loading plates as per the plate map and instructions for 168 plate format OpenArray RT-qPCR assay. The Openarray set using an autoloader loads the Openarray plate which is then run on the OpenArray™ NT cycler to collect data. Each 168-format OpenArray plate can estimate the expression of up to 168 transcripts/genes for 16 samples and three OpenArray plates can be run together on the cycler. The expression of the transcripts in GBM samples as fold changes was calculated relative to normal brain tissue using POLR2A as the normalization control based on the deldelct method.

iii. Analysis of RT-qPCR Results

As illustrated in FIG. 8, the PCR data was added to the PCR data matrix as the 207$^{th}$ row. The PCR data matrix is the data of 206 rows and 121 columns. Rows represent patients and columns represent Transcript IDs. Each entry in this matrix is a fold-change value (ratio of expression of a transcript in a patient sample over the expression of that transcript in normal brain) for the Xth transcript and Yth patient.

Thereafter, as shown in FIG. 8, the data is discretized, the classifier is applied and the probability for the sample to belong to each of the four subtypes is generated.

Example 2: Extensive Isoform-Level Changes Occur in the GBM Transcriptome

Unprocessed exon-array expression data and clinical details for 419 GBM and 10 normal brain samples were downloaded from the TCGA data portal. A subset of 173 GBM samples, marked as "core samples," was further stratified by the method of Verhaak et al[3] into one of the four molecular groups (namely, neural-N, proneural-PN, mesenchymal-M, and classical-CL) (data not shown). The transcript (isoform)-level and gene-level expression estimates were obtained for a total of 114,930 different transcript-variants that correspond to 35,612 different gene models (Ensembl database, version 56). While the comparative statistical analysis between GBM and normal brain at the gene-level produced 2,834 genes as differentially expressed, similar analysis at the isoform-level revealed that a total of 7,313 transcript-variants that correspond to 4,215 genes were significantly altered in GBMs (q≤0.001 and fold-change ≥2.0).

The following Table 3 shows transcriptome analysis at the isoform-level, e.g., the number of up- and downregulated genes or transcripts identified in the The Cancer Genome Atlas (TCGA) GBM cohort's exon-array data.

TABLE 3

TCGA Exon-array Data Analysis

| Response of Gene | Gene Level | Isoform (transcript variant) level |
|---|---|---|
| Upregulated | 912 | 2085 |
| Downregulated | 1922 | 5228 |

The number of genes that are misregulated at the gene-level alone was found to be 174, at the isoform-level alone was found to be 1555. The number of genes that are misregulated at both levels are 2660. We also observed that the transcript-variants of 44 genes (e.g. RTN3, DCLK2, AAK1, ACTN1), primarily associated with cellular assembly and organization, frequently showed opposite patterns of gene isoform expression in GBMs compared to normal brain, with one isoform being upregulated and another isoform of the same gene is downregulated. We validated the isoform-level expression changes by RT-qPCR in primary GBM samples from human brain tumor tissue bank (HBTTB) at The University of Pennsylvania (Penn) for 15 of 16 isoform transcripts corresponding to 6 genes. This shows that the isoform-level expression patterns obtained by analyzing TCGA exon-array datasets can be validated across a cohort of independent GBM patient samples (data not shown) using an independent assay. Since, for a large number of genes, we observed significant expression differences at the isoform-level but not at the overall gene-level, we investigated whether the transcriptome changes at the isoform-level can provide better GBM stratification in terms of overall prognosis and classification accuracy in the TCGA GBM cohort. The scheme that was followed for building an isoform-based classifier for GBM patient, including subtyping and translating the classifier to a clinically applicable GBM diagnostic assay included the steps in order of:

TCGA GMB cohort exon array data→Isoform level, expression-based molecular subtypes→Build a classifier; select set of isoforms→Translate classifier to an RTqPCR-based assay→Test and validate the RT-qPCR based assay→Diagnostic assay to identify GBM subtype.

Figure 5:
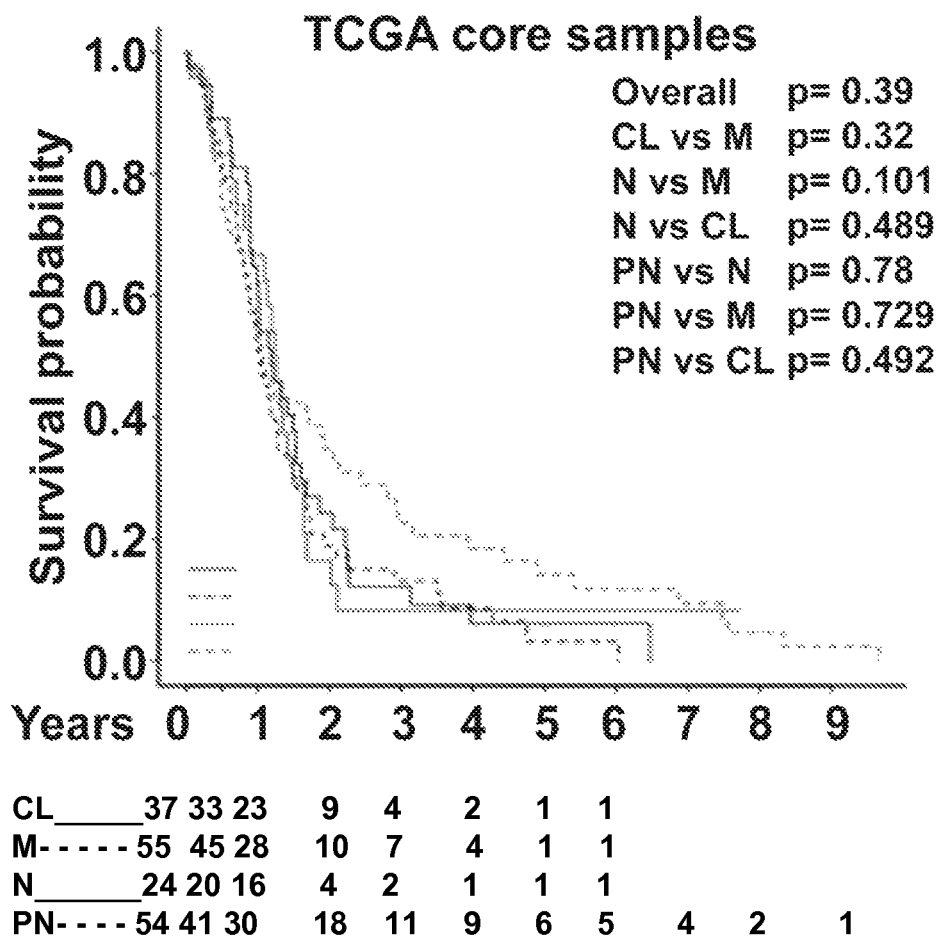
FIG. 5 is a Kaplan-Meier survival curve showing the TCGA classification of GBM patients into 4 groups using the known 804 gene based classifier.
Figure 6:
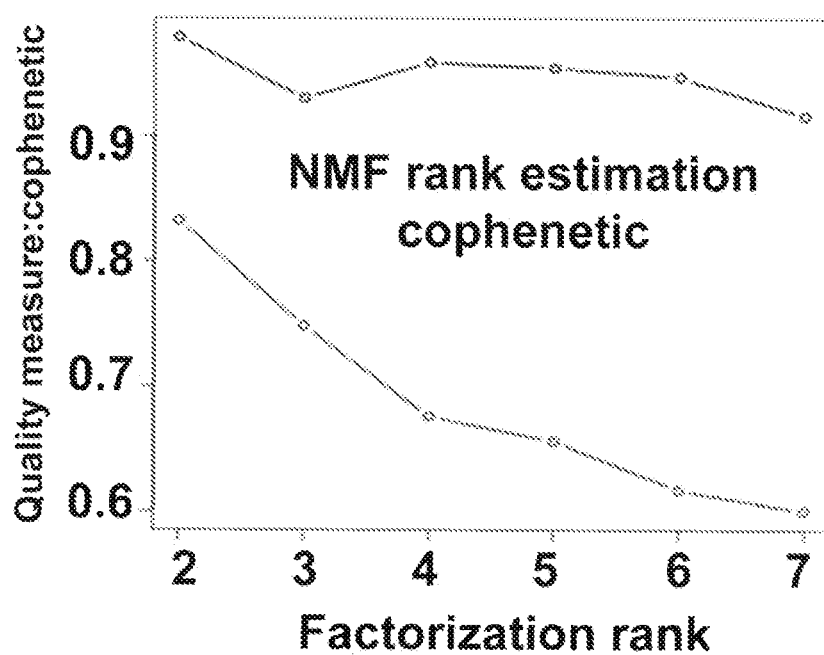
FIG. 6 is a graph showing that stable clustering at the isoform level can be achieved in four groups, using isoform expression data of 197 samples and 1600 isoforms with the highest variability across patients using the coefficient of variation, plotting a cophenetic quality measure vs. factorization rank.

Example 3: Isoform-Level Gene Expression Signatures Show Improved Predictive and Prognostic Value in GBM Patient Stratification Although the TCGA core samples were divided into one of four subtypes—N, PN, M, and CL—based on the gene-level expression signature of 840 genes, no statistically significant survival differences were observed between the subtypes (See FIG. 5)[3]. Since the isoform-level expression analysis captured significantly more transcriptome changes than the gene-level analysis, we evaluated the clustering of GBM samples by using the isoform-level expression profile. We first selected the most-variable transcript-variants across the tumor samples and performed consensus non-negative matrix factorization (NMF) clustering to stratify GBM patient samples. We identified four major clusters, hereafter called "isoform-based groups," using the expression of 1,600 of the most variable transcripts (See FIG. 6). The NMF-based clustering based on the data of FIG. 6 is not shown.

We identified the four GBM groups as "proneural," "mesenchymal," "classical," and "neural," based on the concordance in cluster membership calls between the isoform-based and gene-based groupings in the TCGA publication[3]

An isoform-level, expression-based clustering of GBM patients from the TCGA cohort, shown as a non-negative matrix factorization (NMF)-method-based clustering of 419 GBM patient samples based on the expression of 1,600 of the most variable transcripts/isoforms across the patients was shown as FIG. 2A in the parent US provisional application. Four clusters were formed, and on top, the distribution of 173 TCGA core samples in each cluster was shown. The subtypes of the TCGA core samples are proneural-PN, mesenchymal-M, neural-N, and classical-CL (data not shown).

In order to prepare homogeneous, isoform-based GBM subgroups, we filtered out samples that were not good representatives of a subgroup by employing the silhouette width method.[22]

Table 4 is a concordance table showing the comparison of TCGA's core sample assignment to four subtypes based on gene-level (Verhaak et al.[3]) and isoform-level expression (isoform-based clustering).

TABLE 4

| | | Gene based clustering (Verhaak et al) | | | | |
|---|---|---|---|---|---|---|
| | | PN | N | CL | M | Total |
| Isoform-based clustering | PN | 43 | 2 | 1 | 0 | 46 |
| | N | 4 | 25 | 10 | 6 | 44 |
| | CL | 2 | 0 | 25 | 2 | 28 |
| | M | 2 | 1 | 5 | 44 | 51 |
| | Total | 48 | 28 | 41 | 52 | 169 |

This resulted in the removal of 77 samples, leading to a final set of 75 neural (N), 95 proneural (PN), 85 mesenchymal (M), and 87 classical (CL) GBM samples—for a total of 342 as most representative of the four groups, hereafter called "isoform-based core samples." Among the 169 common to both TCGA and isoform-based core samples (Table 4), 32 (19%) were reassigned to a different subgroup by the described isoform-based signature. Surprisingly, the switching of these few GBM samples resulted in the PN subgroup to have statistically significant better survival (FIGS. 1A, 1B and 2).

To develop a diagnostic test for predicting the subtype of a GBM patient, we built a four-class classification model by using the isoform-based core samples as the training set. In order to translate the classification model that was trained on data from one platform (exon-array) to data from an independent platform (RNA-seq or RT-qPCR), we applied a data discretization method for converting continuous data values into categorical data.[23]

Briefly described the application of data discretization to build a new classifier based on Liu H et al[23] follows the steps:

First, the expression values of each transcript across all the samples in one platform are sorted in ascending order. Then the resulting sorted vector is discretized into a predetermined number of bins b (b+20). Each bin has equal size. Every expression value is replaced by an integer value corresponding to the rank of the bin it falls into. The formula is:

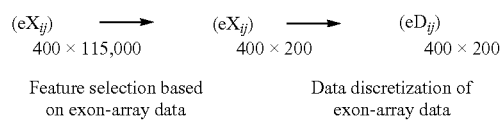

-continued $$(pD_{ij}) \longleftarrow (pY_{ij})$$
$$00 \times 200 \quad 400 \times 200$$

Data discretization of
RT PCR data.

We discretized the fold-change levels (GBM over normal brain) of each transcript expression into different numbers of categories (with equal bin sizes) to determine if finer or coarser discretization improves classification accuracy. Prior to building the classification model, we applied a random-Forest-based variable selection algorithm[20] to select a small set of non-redundant genes or isoforms, using discretized gene-level or isoform-level expression fold-changes, respectively. We first compared the prediction accuracy of a gene-based versus an isoform-based classifier to correctly call the subtype of a GBM sample, and found that the isoform-based classifier is better both in terms of numbers of variables (genes/isoforms) required and prediction accuracy (See FIG. 3A).

For example, while the isoform-based randomForest model achieved 90% accuracy with as few as 50 isoforms as feature variables, the gene-based model required more than 100 genes as feature variables for comparable accuracy to the isoform-based model. By selecting 214 transcripts/isoforms (Table 1) as the most discriminative feature variables between the four GBM subgroups, we created a random-Forest classifier, based on isoform-level expression, for subtype prediction. Using the 214 transcript variants as the number of variables/features selected by RandomForest feature selection, with an OOB error rate; and error rate based on independent test set of 0.063, using 4 housekeeping genes Polr2a, GAPDH, B2M, and B-Action; 147 variable transcripts with 18 non-coding transcripts (8 were consistently up; 8 were consistently down), the RandomForest algorithm discovered sets of isoforms that are most discriminative between the four sub-groups of GBMs. In one example, the six most discrimination transcripts were: ENST00000448418; ENST00000259056; ENST00000470802; ENST00000233946; ENST00000441301 and ENST00000225441. The accuracy of the final selected classifier based on cross-validation analysis (leave-one-out or out-of-bag [OOB] approach) is 93.6%.

We further tested the classifier by dividing the isoform-based core samples into ¾th as training-set and ¼th as test-set. The classification model generated with the use of data from the training set was applied to the test set. The results of this independent testing agreed with those of the leave-one-out cross-validation analysis in 99% of the sample calls in the test set, confirming that the algorithm effectively distinguishes the four GBM subgroups. Many interesting genes that reflect molecular differences between the four GBM subgroups were selected among the 214 isoforms, for example, EGFR, known to be highly amplified in the CL subgroup,[3,24] and MET, a gene associated with epithelial to mesenchymal transition.[25]

Example 4: Translation of Isoform-Level Gene Panel to Clinically Translatable Platform and Validation of the Classifier on Two Independent Cohorts of GBM Patient Samples Since the isoform-based classifier has achieved a prediction accuracy of >90% with fewer numbers of transcripts than the gene-based classifier, we decided to translate the isoform-level gene panel (214 transcripts) to an RT-qPCR-based assay for a clinically applicable diagnostic test. We used the OpenArray Real Time PCR platform (Life Technologies Corporation) to perform the RT-qPCR assay for selected transcripts and tested it on an independent cohort of GBM tumor tissues. Because we observed that the accuracy of the classifier did not vary significantly whether we chose as few as 100 isoforms or as many as 214 isoforms in the classification model (~3% decrease for the 100-transcript model compared with the 214-transcript model), we selected the 126 most reliable transcript assays from the commercially available TaqMan chemistry-based qPCR assays. In addition, we included assays for 15 control transcripts (8 up- and 7 downregulated) that are differentially expressed in most GBM samples when compared to normal brain transcriptome. We then tested the customized high-throughput RT-qPCR assay on an independent cohort of 206 primary GBM tumor tissues obtained from Penn (data not shown). We observed that the qPCR assays for 5 out of 126 transcripts failed and so removed them from further analysis. We retrained the classifier with 121 transcripts (identified as targets in Table 1) on isoform-based core samples from TCGA and found a prediction accuracy loss of only 1.5%.

As a first step, we evaluated the transition of the classifier from exon-array to an independent platform by applying on 155 RNA-seq samples downloaded from the TCGA dataportal. Based on 76 GBM samples that overlapped with the isoform-level core samples and were profiled by both exon-array and RNA-seq methods, we found that the classifier made 90% similar sub-type calls between the two platforms, and achieved 93% prediction accuracy when compared with the true-class labels (data not shown). Therefore, the classifier trained on discretized fold-change data provided a platform independent isoform-level gene signature with a high degree of concordance and prediction accuracy.

Next, we tested the classifier on the Penn cohort of GBM patient samples, by using the RT-qPCR based assay designed above. First, we analyzed the concordance between the expression estimates, in terms of fold change relative to normal, obtained from exon-array and RT-qPCR assays. We observed similar expression patterns for 14 of the 15 control transcripts between RT-qPCR and exon-array data analysis (data not shown). To evaluate the data correlation between the two platforms, mean fold changes of 121 transcripts between the TCGA and Penn cohorts were plotted and compared (FIG. 3B). The strong linear relationship between the two datasets indicates that the classifier built on expression data from the exon-array platform can be translated to another independent platform-RT-qPCR, and isoform-level expression patterns for GBM patients is comparable across independent cohorts of patients.

We applied the retrained classifier on the 206 GBM patient samples to identify each patient subtype. For each sample, the classifier calculates the probabilities that it belongs to one of the four subtypes, and the algorithm assigns the sample to the subtype with the highest probability (data not shown). The described results indicate that 52 (25.2%), 41 (19.9%), 50 (24.2%), and 63 (30.5%) of GBM patients belong to PN, N, M, and CL groups, respectively. A closer look revealed that for about 16 (~8%) samples, the difference in the top two probabilities for subtype assignment is less than 0.05%, which we defined as "low-confidence." However, for these samples the described classifier can confidently eliminate the assignment to the other two subtypes. Most of these ambiguous cases involve a decision between neural versus proneural (7/16) and neural versus classical (4/16).

To address the issue of reproducibility, we independently re-isolated RNA and performed the RT-qPCR analysis on three of the GBM patient samples and found good correlation (r~0.9) between the two RT-qPCR datasets. Moreover, when the described classification algorithm was applied, all three samples were assigned to the same subtype as before (data not shown). To further validate the assignment of subtypes, we looked at the expression of known markers for each subtype.[26] As expected, we observed higher expression of the neural marker GABRA1, proneural marker DCX, mesenchymal markers CHI3L1 and MET, and classical marker NES in samples belonging to the N, PN, M, and CL subtypes, respectively (see FIG. 3C).

In conclusion, we have developed an RT-qPCR-based assay that can reproducibly predict the molecular subtype of GBM patients based on the relative expression of only 121 transcripts/isoforms in the tumor tissue.

Figure 4B:
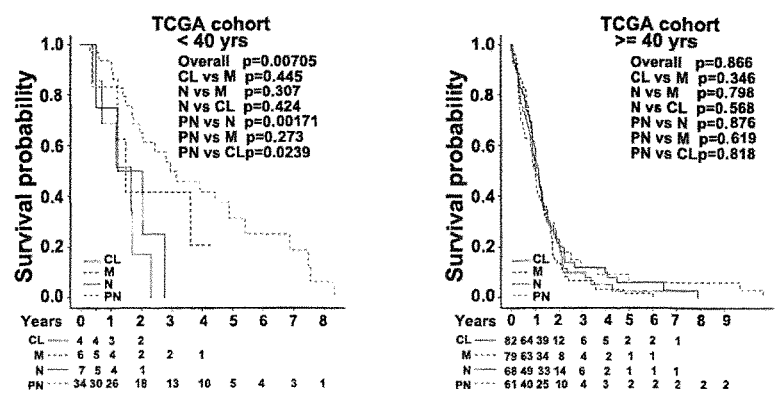
FIG. 4B are two Kaplan-Meier survival plots for isoform-based core samples from TCGA cohort of GBM patients divided by age as <40 yrs and ≥40 yrs at time of diagnosis. The statistical significance of each plot is indicated.

Example 5: Prognostic Significance of the GBM Subtypes and the Contribution of Other Factors to Better Prognosis The molecular stratification of the TCGA GBM cohort by the isoform-based gene signature showed that the PN subgroup has significantly better overall survival than the other three groups. We plotted the survival curves for the four predicted groups of the Penn GBM cohort. However, to the inventors' surprise, we did not observe a better overall survival for the PN group. Instead, we found that the neural group had a significantly better survival rate compared to the classical and mesenchymal subtypes, a difference that remained significant even after the patient samples with low-confidence subtype scores were omitted (FIG. 4A and data not shown). This result prompted us to investigate the characteristic difference between the two cohort populations (Table 5).

found that most of the younger GBM patients in the TCGA cohort were classified as PN (34/51), and these patients had much longer survival compared to the older PN patients (Table 6 and FIG. 4B).

TABLE 6

Distribution of GBM patients by age at diagnosis below and over 40 yrs and the representation of female and male patients among them in each of the four subtypes.

|  |  | TCGA samples | | | | Penn samples | | | |
|---|---|---|---|---|---|---|---|---|---|
|  |  | PN | N | CL | M | PN | N | CL | M |
| Overall |  | 95 | 76 | 86 | 85 | 52 | 41 | 63 | 50 |
| Age < 40 yrs |  | 34 | 7 | 4 | 6 | 6 | 1 | 4 | 0 |
| Gender | Male | 14 | 4 | 0 | 1 | 4 | 1 | 2 | 0 |
|  | Female | 20 | 3 | 4 | 5 | 2 | 0 | 2 | 0 |
| Age > 40 yrs |  | 61 | 69 | 82 | 79 | 46 | 40 | 59 | 50 |
| Gender | Male | 39 | 48 | 47 | 51 | 32 | 19 | 30 | 34 |
|  | Female | 22 | 21 | 35 | 28 | 14 | 21 | 29 | 16 |

TABLE 5

Distribution of GBM patients in the two cohorts based on age.

| TCGA samples | | | | | Penn samples | | | | |
|---|---|---|---|---|---|---|---|---|---|
| Age group (yrs) | | | | | | | | | |
| <40 | 40-50 | 51-60 | 61-70 | >70 | <40 | 40-50 | 51-60 | 61-70 | >70 |
| Patient (%) 14.62 | 16.37 | 26.02 | 26.6 | 14.91 | 5.78 | 18.42 | 25.78 | 25.78 | 22.1 |

One striking difference was in the representation of younger GBM patients (<40 yrs old at the time of diagnosis) between the two cohorts; 27 while 14.6% in TCGA were younger, only 5.8% were younger in the Penn cohort. We Another interesting observation was that the survival among the younger TCGA patients in the PN group from the MD Anderson collection center was almost twice that of the young PN patients from the other centers (Table 7).

TABLE 7

Distribution of patients in the TCGA cohort younger than 40 yrs from MD Anderson and other centers and their average survival for the four subtypes.

|  | PN | | N | | CL | | M | |
|---|---|---|---|---|---|---|---|---|
|  | MD-A | Others | MD-A | Others | MD-A | Others | MD-A | Others |
| Patient no. | 15 | 19 | 2 | 5 | 2 | 5 | 1 | 6 |
| Avg. survival (days) | 1520 | 748 | 431 | 510 | 736 | 561 | 492 | 583 |

Figure 4C:
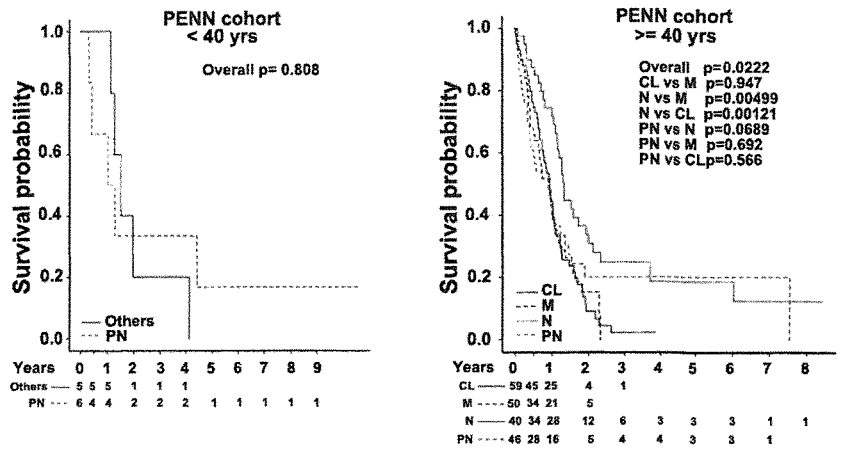
FIG. 4C are two Kaplan-Meier survival plots for isoform-based core samples from Penn cohort of GBM patients divided by age as <40 yrs and ≥40 yrs at time of diagnosis. The statistical significance of each plot is indicated.

Hence, we decided to re-plot the survival curves for the TCGA and Penn cohorts separately for younger (<40 years) and older patients (>40 years) (FIGS. 4B and 4C).

Our results clearly demonstrate that the prognostic significance of the PN group in terms of survival is valid only for the younger patients, and among the older patients, the PN group has the poorest six-month survival rate in both the TCGA and Penn cohorts (Table 8).

TABLE 8

Comparison of survival among the TCGA cohort and Penn cohort of GBM patients (≥40 yrs) belonging to the four subtypes

| Survival | TCGA cohort (%) | | | Penn cohort (%) | | |
|---|---|---|---|---|---|---|
| (months) | 6 | 12 | 24 | 6 | 12 | 24 |
| N | 72.0 | 47.8 | 20.5 | 85.0 | 70.0 | 30.0 |
| PN | 65.5 | 41.0 | 16.4 | 60.8 | 34.7 | 10.9 |
| M | 79.5 | 43.6 | 10.3 | 68.0 | 42.0 | 10.0 |
| CL | 77.2 | 46.8 | 15.2 | 76.2 | 42.3 | 6.8 |

Among the older GBM patients, the neural group shows significantly better survival in the Penn cohort and, in general, the longer-surviving (more than two years after diagnosis) N patients tend to be older than 50 years, unlike the longer-surviving PN patients who tend to be younger (FIG. 4C). Also worth noting is the difference between survival of the Penn N and TCGA N groups. While the six-month survival rate is quite similar between the two groups, the one-year survival rate for the Penn N group is significantly higher (70% of patients were alive after one year post-treatment) than the TCGA N group (only 48% of patients were alive after one year post-treatment) (Table 8). While most patients grouped in the TCGA PN, M, and N groups were males, only the PN and M groups in the Penn cohort had a higher representation of males. Interestingly, a small proportion of GBM patients (5.6% in the Penn cohort and 7% in the TCGA cohort) survived for at least three years, and most of the patients in the Penn cohort belonged to either the PN or N subtype, whereas in the TCGA cohort they were distributed across all four subtypes (FIGS. 4B and 4C).

Based on the results described above, this analysis agrees with the GBM field's general belief that patients who are young and have a PN subtype tend to have better prognoses.[28] We also found that with the current standard therapy available for the disease, older patients with the PN subtype have a poor prognosis, while the best prognosis is for the N group of patients.

Example 6: Analysis Using Modified PIGExClass

Having established a prognostic stratification of GBM samples based on isoform-level gene expression clustering, we sought to (1) design a universal classification model that will be independent of the gene expression measuring platform, and (2) identify a small subset of genes or isoforms that are discriminatory between the four subgroups. To determine the type of the classification variable (genes vs isoforms), we compared the prediction accuracy of a gene-based versus an isoform-based classifier to correctly call the subtype of a GBM sample, and found that the isoform-based classifier is better both in terms of numbers of variables (genes/isoforms) required and prediction accuracy (FIG. 3A). For example, while the isoform-based randomForest model achieved 90% accuracy with as few as 50 isoforms as feature variables, the gene-based model required more than 100 genes as feature variables for comparable accuracy to the isoform-based model. We also evaluated the performance of gene-based classifier vs isoform-based classifier when the initial NMF cluster identification was performed using the gene-level expression (data not shown; provided as Supplementary Figure S3[46]). Even in this scenario, an isoform-based classifier had a better performance than the gene-based classifier. In the final "classification" step, by selecting 213 transcripts/isoforms as the most discriminative variables between the four GBM subgroups, a randomForest classifier is built for subtype prediction.

The accuracy of the final selected classifier based on cross-validation analysis (out-of-bag [OOB] approach) is 93.6%. The classifier was further tested by dividing the isoform-based core samples into $\frac{3}{4}^{th}$ as training-set and $\frac{1}{4}^{th}$ as test-set. The classification model generated from the training set was applied to the test set. The results of this additional testing agreed with those of the OOB approach in 99% of the sample calls in the test set, confirming that the algorithm effectively distinguishes the four subgroups. We also compared the error rate with and without discretization on the training data set and find that the OOB error rate decreases from 8.6% to 6.4% after discretization, suggesting that data discretization is not only critical for platform transition but also important for classifier's accuracy within the same platform. Genes that reflect molecular differences between the subgroups were selected among the 213 isoforms, for example, EGFR, known to be highly amplified in the CL subgroup[13,32], and MET, a gene associated with epithelial to mesenchymal transition[47].

A. Translation of Isoform-Level Gene Panel to Clinically Translatable Platform and Validation of the Classifier Since the isoform-based classifier from PIGExClass has achieved a prediction accuracy of >90% with fewer numbers of transcripts than the gene-based classifier, we decided to translate the classifier's isoform-level gene-panel (213 transcripts) to an RT-qPCR-based assay. Because we observed that the accuracy of the randomForest classifier did not vary significantly whether we chose as few as 100 isoforms or as many as 213 isoforms in the classification model (FIG. 3A, ~3% decrease in accuracy), we selected the 121 most reliable commercially available TaqMan chemistry-based qPCR assays, and translated these transcript assays to RT-qPCR platform (Table 1). We retrained the classifier with 121 transcripts on isoform-based core samples from TCGA and found a prediction accuracy loss of only 1.5%.

As a first step, we evaluated the transition of the classifier from exon-array to an independent platform by applying on 155 RNA-seq TCGA samples. We found that the data discretization with equal-frequency binning gave better classification accuracy than that based on equal-width binning We, therefore adopted the data-discretization with equal frequency binning for data transition across platforms. Based on 76 GBM samples that overlapped with the isoform-level core samples and were profiled by both exon-array and RNA-seq methods, we found that the classifier made 90% similar sub-type calls between the two platforms, and achieved 93% prediction accuracy when compared with the true-class labels (Supplemental Table S4[46] and Table 9 below).

Table 9 shows the confusion matrix when the classifier was applied on the RNA-seq data for the 76 GBM patients from TCGA for who exon-array expression data was also available.

|  |  | Predicted labels | | | | |
|---|---|---|---|---|---|---|
|  |  | N | PN | M | CL | Class Error |
| True | N (22) | 16 | 1 | 1 | 6 | 0.27 |
| Labels | PN (18) | 0 | 18 | 0 | 0 | 0.00 |
|  | M (20) | 0 | 0 | 20 | 0 | 0.00 |
|  | CL (16) | 0 | 0 | 0 | 16 | 0.00 |

However, the classifier's accuracy was only 66% on these 76 GBM samples if data discretization step was omitted. The stability in the classification accuracy across the two platforms is primarily due to reduced variability in FCCVs and increased correlation across platforms (FIG. 3B). Therefore, the classifier trained on discretized fold-change data provided a platform independent isoform-level gene signature with a high degree of concordance and prediction accuracy.

Next, we tested the classifier on the Penn-cohort of 206 samples, by using the RT-qPCR based assay designed above. First, we analyzed the concordance between the expression estimates, in terms of fold change relative to normal, obtained from exon-array and RT-qPCR assays. We observed similar expression patterns for 14 of the 15 control transcripts between RT-qPCR and exon-array data analysis, as shown in Table 10. The top 8 and bottom 7 transcripts represented the selected up- and down-regulated transcripts respectively.

TABLE 10

Exon Array And RT-PCR Data Agree In Expression Of Up And Down-Regulated Transcripts

| Transcript ID | Gene | Median Fold Changes (GBM/Normal) | |
|---|---|---|---|
|  |  | Exon array 9TCGA) | RT-qPCR (HBTTB cohort) |
| ENST00000373020 | TSPAN6 | 3.1 | 12.0 |
| ENST00000218340 | RP2 | 2.7 | 5.6 |
| ENST00000483967 | EZH2 | 2.9 | 17.8 |
| ENST00000263635 | TANC1 | 2.7 | 5.6 |
| ENST00000450318 | NUSAP1 | 2.7 | 6.1 |
| ENST00000411739 | NEDD1 | 2.7 | 2.3 |
| ENST00000478293 | MKI67 | 2.6 | −2.4 |
| ENST00000295633 | FSTL1 | 2.6 | 6.6 |
| ENST00000389722 + ENST00000389723 | SPTB | −7.1 | −9.6 |
| ENST00000381142 | TYRP1 | −6.9 | −17.9 |
| ENST00000369777 | NEURL | −14.4 | −17.7 |
| ENST00000414191 + ENST00000439163 | PLCH1 | −5.2 | −1.5 |
| ENST00000262450 | CHD5 | −5.2 | −15.6 |
| ENST00000322893 | KCNH5 | −5.4 | −26.0 |
| ENST00000304045 | KLK7 | −5.0 | −3496.5 |

To evaluate the data correlation between the two platforms, mean fold changes of 121 transcripts between the TCGA and Penn-cohorts were plotted and compared (FIG. 3C). The strong linear relationship between the two datasets indicates that the classifier built on expression data from the exon-array platform can be translated to RT-qPCR platform, and isoform-level expression patterns for GBM patients is comparable across independent cohorts of patients.

Figure 11:
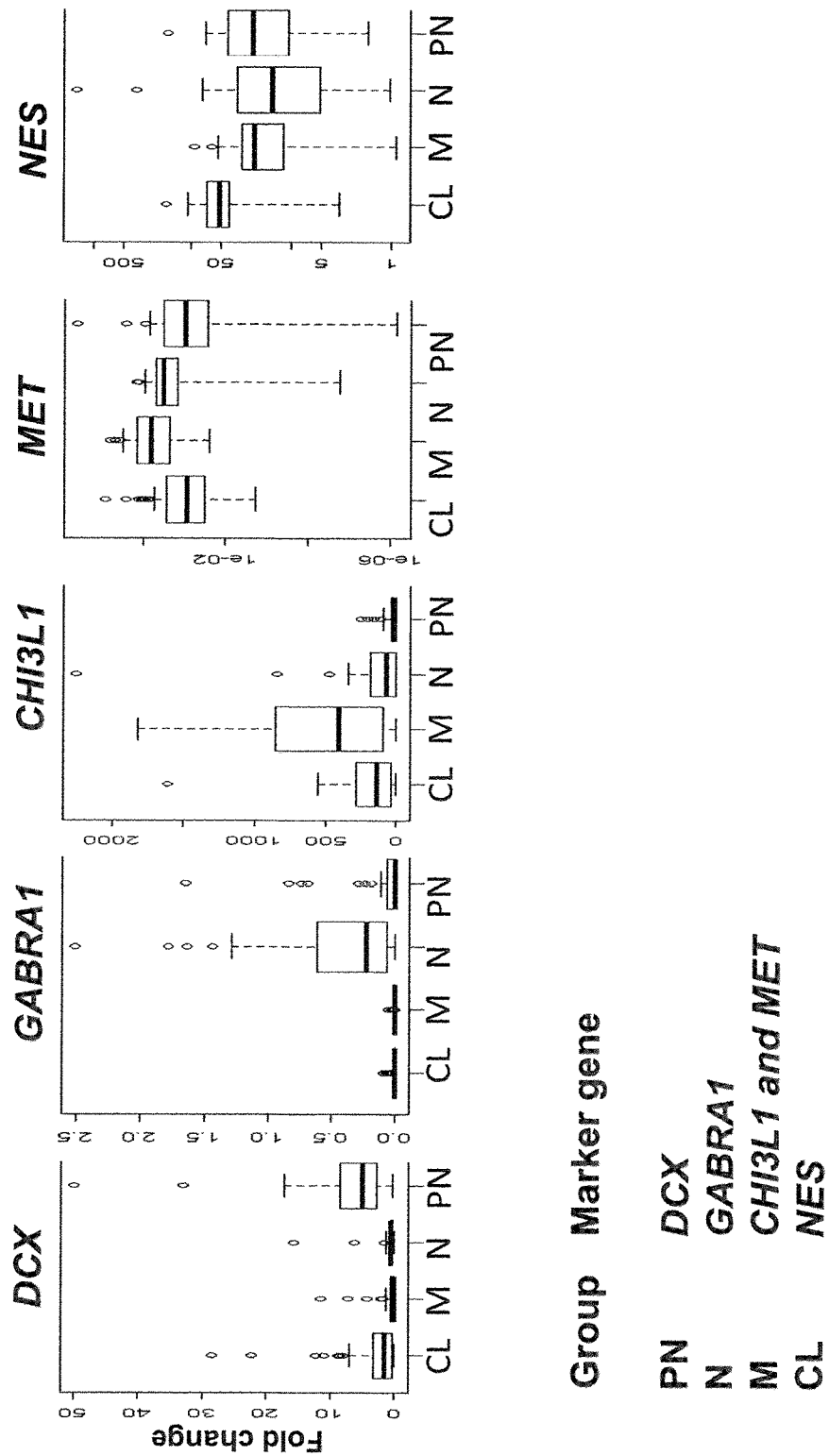
FIG. 11 is a series of boxplot graphs showing subtype specific marker gene expression in the TCGA cohort profiled by RNA-sequence. Each boxplot represents the expression as fold change from RNA-seq data for the marker genes of the four different subtypes in TCGA-cohort of GBM patients (155) identified by the 121 isoform classifier. The y-axis for MET is shown in logarithmic scall. All fold changes were calculated relative to normal brain tissue and statistical significance was determined by two sample t-test.
Figure 12:
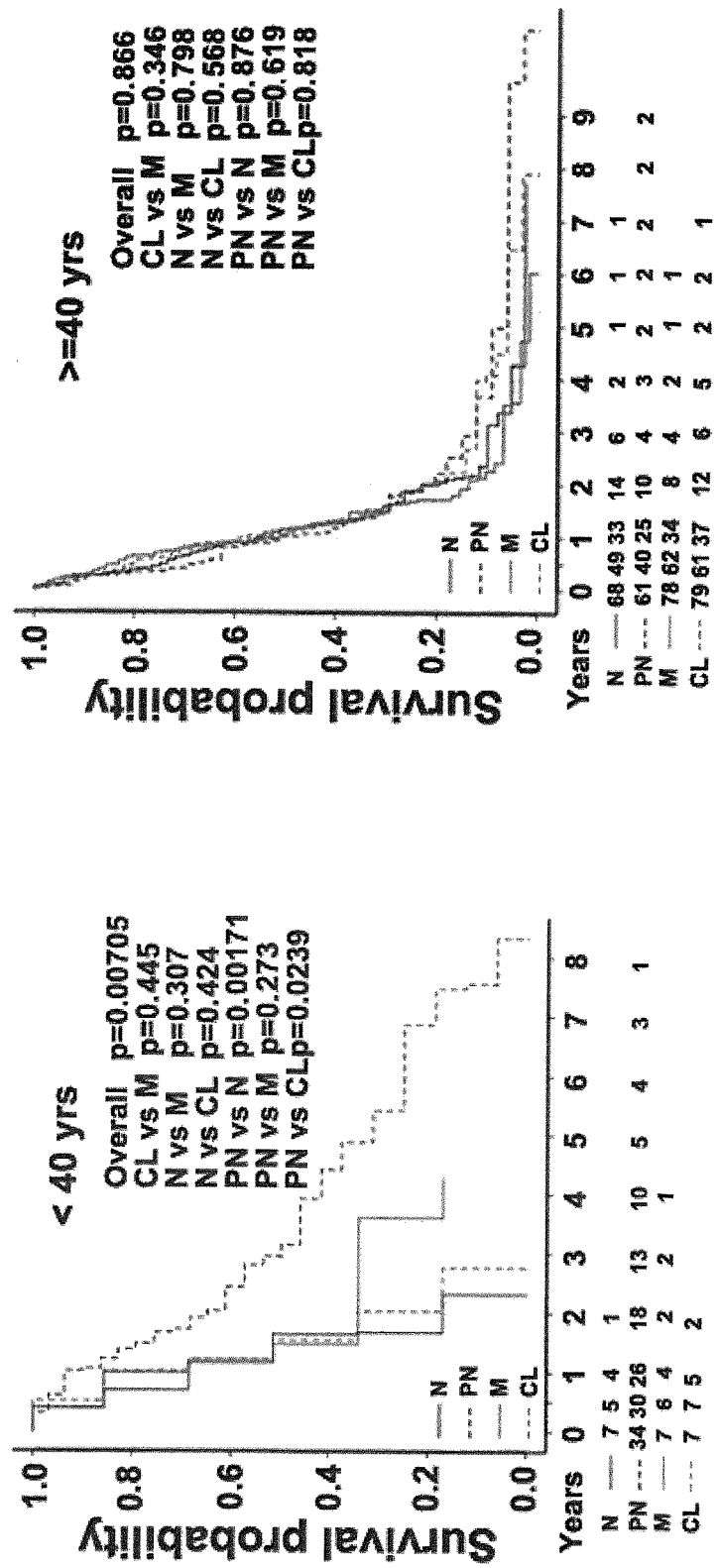
FIG. 12 are two survival plots (left panel and right panel) on the TCGA cohort segregated by age; left panel is patients less than 40 years of age; right panel is greater than or equal to 40 years of age.
Figure 13:
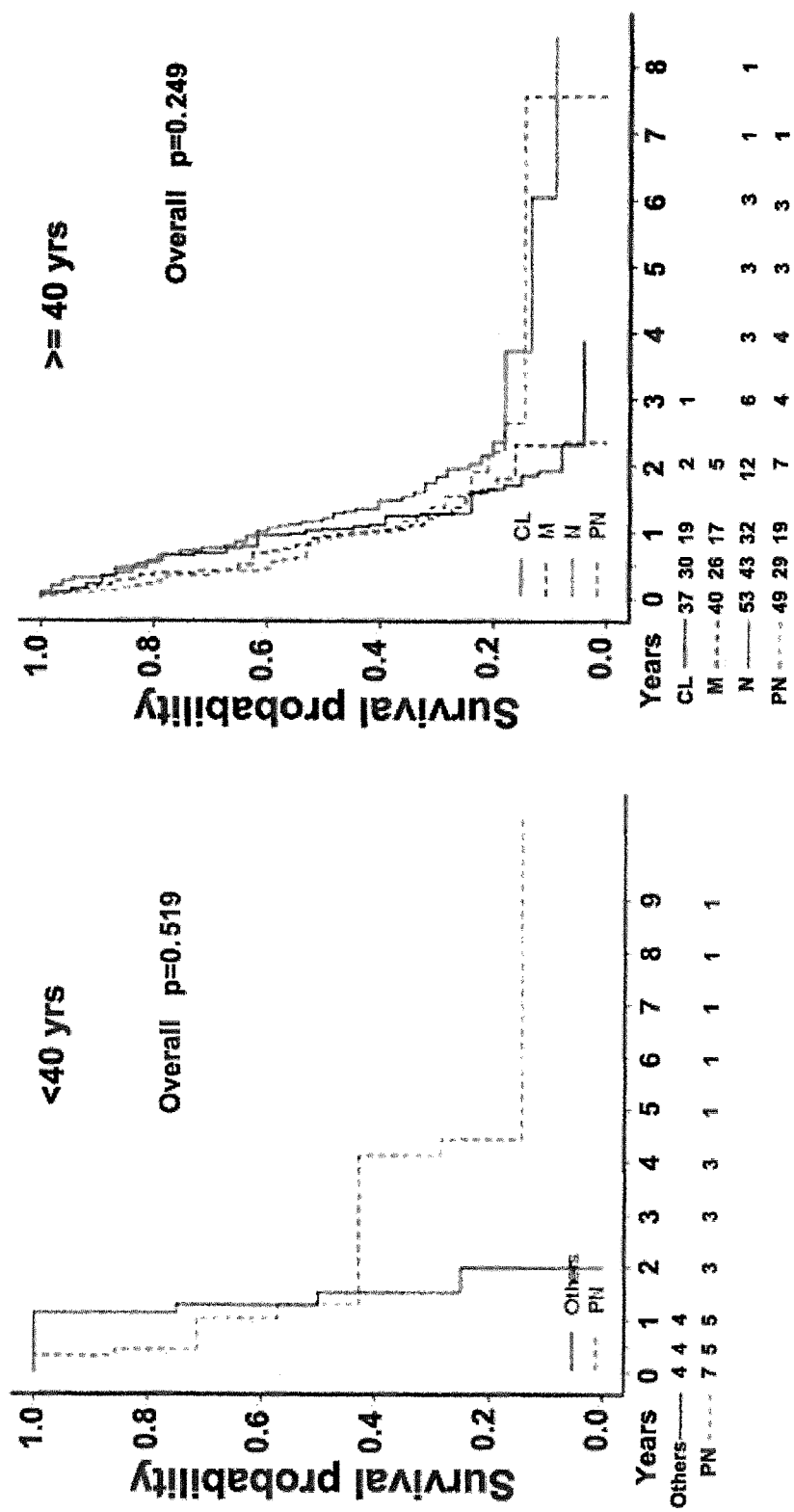
FIG. 13 are two survival plots on the Penn cohort segregated by age; left panel is patients less than 40 years of age; right panel is greater than or equal to 40 years of age.
Figure 14:
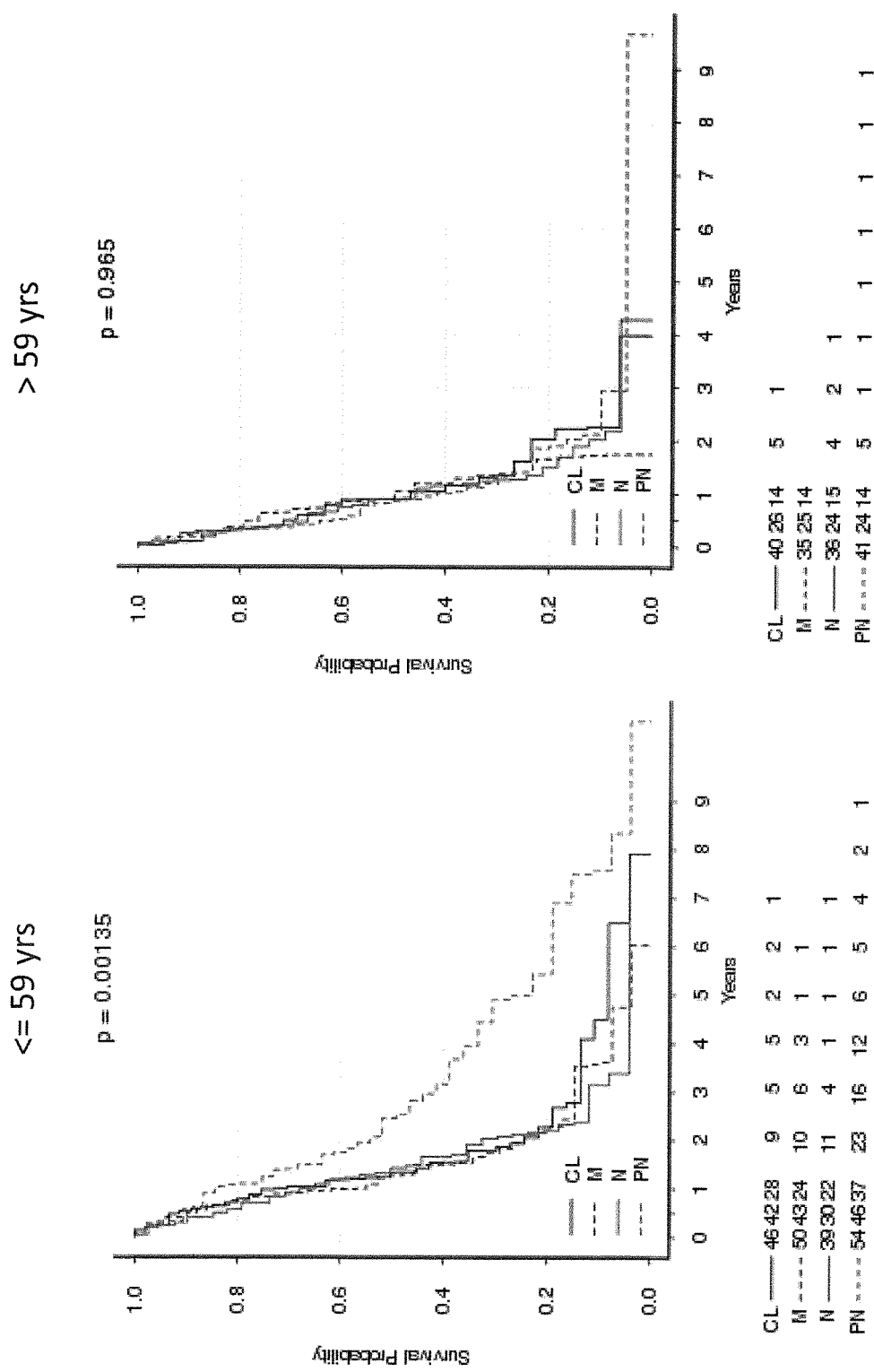
FIG. 14 are two survival probability graphs of TCGA samples separated by median age; left panel is less than or equal to 59 years of age; right panel is greater than 59 years of age.
Figure 15:
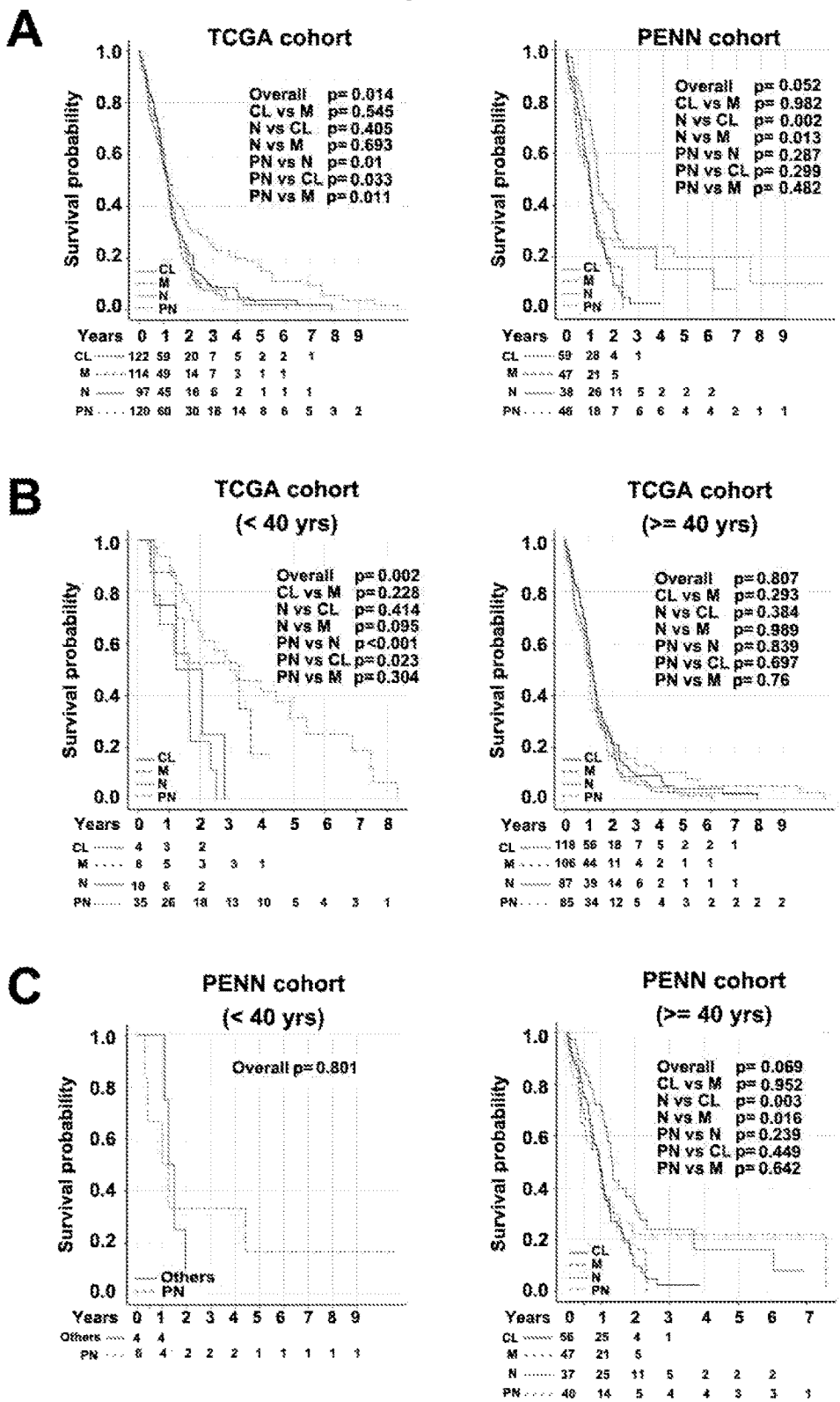
FIG. 15A consists of two updated Kaplan-Meier survival plots for TCGA cohort (left) and Penn cohort (right) of GBM patients with the overall survival curve for GBM patients who were classified into four subtypes by the 121 isoform classifier based on the RT-qPCR expression estimates. The statistical significance of each plot is indicated. These plots were generated using the updated Platform-independent isoform-level gene expression based classification system (PIGExClass).
FIG. 15B consists of two updated Kaplan-Meier survival plots for isoform-based core samples from TCGA cohort of GBM patients divided by age as <40 yrs (left) and ≥40 yrs (right) at time of diagnosis. The statistical significance of each plot is indicated. These plots were generated using the updated Platform-independent isoform-level gene expression based classification system (PIGExClass).
FIG. 15C consists of two Kaplan-Meier survival plots for isoform-based core samples from Penn cohort of GBM patients divided by age as <40 yrs (left) and ≥40 yrs (right) at time of diagnosis. The statistical significance of each plot is indicated. These plots were generated using the updated Platform-independent isoform-level gene expression based classification system (PIGExClass).

We applied the retrained classifier on the Penn-cohort to identify each patient's subtype. Our results indicate that 52 (25.2%), 41 (19.9%), 50 (24.2%), and 63 (30.5%) of patients belong to PN, N, M, and CL groups, respectively (Supplemental Table S7). We also observed that for 16 (~8%) samples, the difference in the top two probabilities for subtype assignment is less than 0.05%, which we defined as "low-confidence". However, for these samples our classifier can confidently eliminate the assignment to the other two subtypes. To address the issue of reproducibility, we independently re-isolated RNA and performed the RT-qPCR analysis on three patient samples and found good correlation (r~0.9) between the two datasets. Moreover, our PIGEx-Class based classification algorithm assigned the samples to the same subtype as before (Supplemental Table S7[46]). To further validate the assignment of subtypes, we looked at the expression of known markers for each subtype[1]. As expected, we observed higher expression of the neural marker-GABRA1, proneural marker-DCX, mesenchymal markers-CHI3L1 and MET, and classical marker-NES in samples belonging to the N, PN, M, and CL subtypes, respectively (FIG. 3D). Similar marker expression pattern was observed for the 155 GBM samples from TCGA that were subtyped based on RNA-seq data (FIG. 11). In conclusion, we have developed an RT-qPCR-based assay that can reproducibly predict the molecular subtype of GBM patients based on the relative expression of only 121 transcripts/isoforms in the tumor tissue.

B. Prognostic Significance of the Stratification in Younger and Older GBM Patients The molecular stratification of the TCGA-cohort's isoform based core samples by the isoform-based signature showed that the PN subgroup has significantly better overall survival than the other three groups (FIG. 2). We plotted the survival curves for the four predicted groups of the whole TCGA-cohort (both exon array and RNA-seq samples) and Penn-cohort after removing the samples with low confidence calls (FIG. 4A). To our surprise, we did not observe a better overall survival for the PN group in the Penn-cohort. Instead, we found that the neural group had a significantly better survival rate compared to the classical and mesenchymal subtypes (FIG. 4A). This result prompted us to investigate the characteristic differences between the two cohorts (Table 11). One striking difference was in the representation of younger patients (age<40 years at diagnosis) between the two cohorts (10); while 12.1% in TCGA-cohort were younger, only 5.8% were younger in the Penn-cohort. We found that most of the younger patients—in the TCGA-cohort were classified as PN (35/57), and these patients had a much longer survival compared to the older PN patients (Table 11 and FIG. 4B). Hence, we decided to re-plot the survival curves for the TCGA and Penn cohorts separately for younger (<40 years) and older patients (40 years) (FIG. 4B, C). Our results clearly demonstrate that the prognostic significance of the PN group in terms of survival is valid only for the younger patients, and among the older patients, the PN group has the poorest six-month survival rate in both the TCGA and Penn cohorts (Table 11).

Based on the results described above, our study agrees with the general consensus that patients who are young and have a PN subtype tend to have better prognoses[11]. We also found that among the older patients, the PN subtype confers a poorer prognosis.

TABLE 11

Updated Distribution of GBM patients in TCGA and Penn cohorts based on age and molecular subtype (earlier analysis in Tables 5, 6, 8).

| Distribution of GBM patients by age | | | | | | | | | |
|---|---|---|---|---|---|---|---|---|---|
| | TCGA sales | | | | | Penn samples | | | |
| | Age group (yrs) | | | | | | | | |
| | <40 | 40-50 | 51-60 | 61-70 | >70 | <40 | 40-50 | 51-60 | 61-70 | >70 |
| Patient (%) | 12.1 | 13.1 | 26.5 | 27.3 | 20.8 | 5.78 | 18.42 | 25.78 | 25.78 | 22.1 |

| Distribution of young and older GBM patients among the four subtypes | | | | | | | | |
|---|---|---|---|---|---|---|---|---|
| | | TCGA samples | | | | Penn samples | | | |
| | | PN | N | CL | M | PN | N | CL | M |
| Overall | | 121 | 99 | 123 | 114 | 46 | 38 | 59 | 47 |
| Age < 40 yrs | | 35 | 10 | 4 | 8 | 6 | 1 | 3 | 0 |
| Gender | Male | 14 | 5 | 0 | 2 | 4 | 1 | 1 | 0 |
| | Female | 21 | 5 | 4 | 6 | 2 | 0 | 2 | 0 |
| Age > 40 yrs | | 86 | 89 | 119 | 106 | 40 | 37 | 56 | 47 |
| Gender | Male | 58 | 61 | 71 | 68 | 29 | 17 | 29 | 32 |
| | Female | 28 | 28 | 48 | 38 | 11 | 20 | 27 | 15 |

| Survival for the older (>40 yrs) GBM patients among the four subtypes | | | | | | |
|---|---|---|---|---|---|---|
| | TCGA-cohort (%) | | | Penn-cohort (%) | | |
| | Survival (months) | | | | | |
| | 6 | 12 | 24 | 6 | 12 | 24 |
| N | 63.2 | 44.8 | 16 | 83.8 | 67.5 | 29.7 |
| PN | 63.5 | 40 | 14.1 | 65 | 35 | 12.5 |
| M | 67.9 | 41.5 | 10.3 | 70.2 | 44.6 | 10.6 |
| CL | 71.1 | 47.4 | 15.2 | 76.7 | 44.6 | 7.1 |

Each and every patent, patent application, and publication, including publications listed below, each publically available nucleotide, oligonucleotide and protein sequences cited throughout the disclosure, U.S. Provisional Patent Application No. 61/808,878, filed Apr. 5, 2013; U.S. Provisional Patent Application No. 61/937,215, filed Feb. 7, 2014; and Pal et al., "Isoform-Level Gene Signature Improves Prognostic Stratification and Accurately Classifies Glioblastoma Subtypes", Nucl. Acids Res., e-publication: Feb. 6, 2014 are expressly incorporated herein by reference in its entirety. Embodiments and variations of this invention other than those specifically disclosed above may be devised by others skilled in the art without departing from the true spirit and scope of the invention. The appended claims include such embodiments and equivalent variations.

REFERENCES

1. Dunn G P, Rinne M L, Wykosky J, et al. Emerging insights into the molecular and cellular basis of glioblastoma. Genes & development 2012; 26:756-84.
2. Vitucci M, Hayes D N, Miller C R. Gene expression profiling of gliomas: merging genomic and histopathological classification for personalised therapy. British journal of cancer 2011; 104:545-53.
3. Verhaak R G, Hoadley K A, Purdom E, et al. Integrated genomic analysis identifies clinically relevant subtypes of glioblastoma characterized by abnormalities in PDGFRA, IDH1, EGFR, and NF1. Cancer cell 2010; 17:98-110.
4. Li A, Walling J, Ahn S, et al. Unsupervised analysis of transcriptomic profiles reveals six glioma subtypes. Cancer research 2009; 69:2091-9.
5. Olson S, Berger A C. Genome-Based Diagnostics: Clarifying Pathways to Clinical Use: Workshop Summary; 2012.
6. Grabowski P. Alternative splicing takes shape during neuronal development. Current opinion in genetics & development 2011; 21:388-94.
7. Pal S, Gupta R, Davuluri R V. Alternative transcription and alternative splicing in cancer. Pharmacol Ther 2012.
8. Bemmo A, Dias C, Rose A A, Russo C, Siegel P, Majewski J. Exon-level transcriptome profiling in murine breast cancer reveals splicing changes specific to tumors with different metastatic abilities. PLoS One 2010; 5:e11981.
9. Boidot R, Vegran F, Lizard-Nacol S. Predictive value of survivin alternative transcript expression in locally advanced breast cancer patients treated with neoadjuvant chemotherapy. Int J Mol Med 2009; 23:285-91.
10. Lapuk A, Marr H, Jakkula L, et al. Exon-level microarray analyses identify alternative splicing programs in breast cancer. Mol Cancer Res 2010; 8:961-74.
11. Misquitta-Ali C M, Cheng E, O'Hanlon D, et al. Global profiling and molecular characterization of alternative splicing events misregulated in lung cancer. Mol Cell Biol 2011; 31:138-50.
12. Wang L, Lawrence M S, Wan Y, et al. SF3B1 and other novel cancer genes in chronic lymphocytic leukemia. The New England journal of medicine 2011; 365:2497-506.
13. Ebert B, Bernard O A. Mutations in RNA splicing machinery in human cancers. New Engl. J. Med. 2011; 365:2534-5.

14. Friboulet L, Olaussen K A, Pignon J P, et al. ERCC1 isoform expression and DNA repair in non-small-cell lung cancer. The New England journal of medicine 2013; 368:1101-10.
15. Turro E, Lewin A, Rose A, Dallman M J, Richardson S. MMBGX: a method for estimating expression at the isoform level and detecting differential splicing using whole-transcript Affymetrix arrays. Nucleic acids research 2010; 38:e4.
16. Workman C, Jensen L J, Jarmer H, et al. A new non-linear normalization method for reducing variability in DNA microarray experiments. Genome biology 2002; 3:research0048.
17. Smyth G K. Linear models and empirical bayes methods for assessing differential expression in microarray experiments. Statistical applications in genetics and molecular biology 2004; 3:Article3.
18. Brunet J P, Tamayo P, Golub T R, Mesirov J P. Metagenes and molecular pattern discovery using matrix factorization. Proceedings of the National Academy of Sciences of the United States of America 2004; 101:4164-9.
19. Gaujoux R, Seoighe C. A flexible R package for non-negative matrix factorization. BMC bioinformatics 2010; 11:367.
20. Diaz-Uriarte R, Alvarez de Andres S. Gene selection and classification of microarray data using random forest. BMC bioinformatics 2006; 7:3.
21. Breiman L. Random Forests. Machine Learning 2001; 45:5-32.
22. Rousseeuw P J. Silhouettes—a Graphical Aid to the Interpretation and Validation of Cluster-Analysis. J Comput Appl Math 1987; 20:53-65.
23. Liu H, Hussain F, Tan C L, Dash M. Discretization: An enabling technique. Data Min Knowl Disc 2002; 6:393-423.
24. Brennan C, Momota H, Hambardzumyan D, et al. Glioblastoma subclasses can be defined by activity among signal transduction pathways and associated genomic alterations. PloS one 2009; 4:e7752.
25. Lu K V, Chang J P, Parachoniak C A, et al. VEGF inhibits tumor cell invasion and mesenchymal transition through a MET/VEGFR2 complex. Cancer cell 2012; 22:21-35.
26. Therneau T M, Grambsch P M. Modeling survival data: extending the Cox model. New York: Springer; 2000.
27. Siker M L, Wang M, Porter K, et al. Age as an independent prognostic factor in patients with glioblastoma: a Radiation Therapy Oncology Group and American College of Surgeons National Cancer Data Base comparison. Journal of neuro-oncology 2011; 104:351-6.
28. Lee Y, Scheck A C, Cloughesy T F, et al. Gene expression analysis of glioblastomas identifies the major molecular basis for the prognostic benefit of younger age. BMC medical genomics 2008; 1:52.
29. Feero W G, Guttmacher A E, Collins F S. Genomic medicine—an updated primer. The New England journal of medicine 2010; 362:2001-11.
30. Poulikakos P I, Persaud Y, Janakiraman M, et al. RAF inhibitor resistance is mediated by dimerization of aberrantly spliced BRAF(V600E). Nature 2011; 480:387-90.
31. McDermott U, Downing J R, Stratton M R. Genomics and the continuum of cancer care. The New England journal of medicine 2011; 364:340-50.
32. Pal S, Gupta R, Kim H, et al. Alternative transcription exceeds alternative splicing in generating the transcriptome diversity of cerebellar development. Genome Res 2011; 21:1260-72.
33. Phillips H S, Kharbanda S, Chen R, et al. Molecular subclasses of high-grade glioma predict prognosis, delineate a pattern of disease progression, and resemble stages in neurogenesis. Cancer cell 2006; 9:157-73.
34. Shen R, Mo Q, Schultz N, et al. Integrative subtype discovery in glioblastoma using iCluster. PloS one 2012; 7:e35236.
35. Sturm D, Witt H, Hovestadt V, et al. Hotspot mutations in H3F3A and IDH1 define distinct epigenetic and biological subgroups of glioblastoma. Cancer cell 2012; 22:425-37.
36. Liang Y, Diehn M, Watson N, et al. Gene expression profiling reveals molecularly and clinically distinct subtypes of glioblastoma multiforme. Proceedings of the National Academy of Sciences of the United States of America 2005; 102:5814-9.
37. Shirahata M, Iwao-Koizumi K, Saito S, et al. Gene expression-based molecular diagnostic system for malignant gliomas is superior to histological diagnosis. Clinical cancer research: an official journal of the American Association for Cancer Research 2007; 13:7341-56.
38. Yan H, Parsons D W, Jin G, et al. IDH1 and IDH2 mutations in gliomas. The New England journal of medicine 2009; 360:765-73.
39. Check Hayden E. Human genome at ten: Life is complicated. Nature 2010; 464:664-7.
40. Tanaka S, Louis D N, Curry W T, Batchelor T T, Dietrich J. Diagnostic and therapeutic avenues for glioblastoma: no longer a dead end? Nature reviews Clinical oncology 2013; 10:14-26.
41. Warnat P, Eils R, Brors B. Cross-platform analysis of cancer microarray data improves gene expression based classification of phenotypes. BMC bioinformatics 2005; 6:265.
42. V C, Roberts A, Goff L, et al. Differential gene and transcript expression analysis of RNA-seq experiments with TopHat and Cufflinks. Nature protocols 2012; 7:562-78.
43. Manilich, E. A., Ozsoyoglu, Z. M., Trubachev, V. and Radivoyevitch, T. (2011) Classification of large microarray datasets using fast random forest construction. *Journal of bioinformatics and computational biology*, 9, 251-267.
44. Datta, S. (2008) Classification of breast cancer versus normal samples from mass spectrometry profiles using linear discriminant analysis of important features selected by random forest. *Statistical applications in genetics and molecular biology*, 7, Article7.
45. Riddick, G. and Fine, H. A. (2011) Integration and analysis of genome-scale data from gliomas. *Nature reviews. Neurology*, 7, 439-450.
46. Pal et al., (2014) "Isoform-Level Gene Signature Improves Prognostic Stratification and Accurately Classifies Glioblastoma Subtypes", *Nucl. Acids Res.*, 1-11, e-publication: Feb. 6, 2014.
47. Zhang, Z., Pal, S., Bi, Y, Tchou, J. and Davuluri, R. V. et al. (Apr. 17, 2013) Isoform-level expression profiles provide better cancer signatures than gene level expression profiles, *Genome Med.*, 5:33.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10113201B2). An electronic copy of the "Sequence Listing" will also be available from the USPTO upon request and payment of the fee set forth in 37 CFR 1.19(b)(3).

The invention claimed is:

1. A kit consisting of ligands that quantitatively detect or identify every one of 121 target isoforms of a glioblastoma (GBM) isoform transcript signature SEQ ID Nos: 1-78 and 95-137, wherein each ligand is a nucleotide or oligonucleotide sequence that binds or hybridizes to a single said target isoform, wherein each ligand is 17 to 30 bases in length, and wherein at least one ligand is covalently joined to a detectable diagnostic label capable of generating a measurable signal; and optionally at least one assay component selected from a substrate for immobilization, a substrate for an enzymatic label, a reagent for conducting an RNA-based assay or an RT-qPCR assay, and computer software.

2. The kit according to claim 1, wherein at least one ligand is covalently attached to a glass or plastic substrate.

3. The kit according to claim 1, wherein each ligand identifies the level of expression or activity of a different target isoform.

4. The kit according to claim 1, wherein each ligand is a PCR oligonucleotide primer or probe, or a pair of PCR oligonucleotide primers or probes that binds to or hybridizes with a single isoform target.

5. The kit according to claim 1, wherein said substrate for immobilization consists of a glass or plastic substrate upon which at least one ligand is covalently attached.

6. The kit according to claim 1, wherein said substrate for immobilization is a microfluidics card, a chip, a bead, or a chamber.

7. A kit consisting of:
(a) ligands that quantitatively detect or identify every one of 121 target isoforms of a glioblastoma (GBM) isoform transcript signature SEQ ID Nos: 1-78 and 95-137, wherein each ligand binds or hybridizes to a single said target isoform, wherein each ligand is 17 to 30 bases in length, and wherein at least one ligand is covalently joined to a detectable diagnostic label;
(b) at least one ligand that binds to, or hybridizes specifically to, a single control or housekeeping gene sequence of SEQ ID NOs: 79 to 94; and
(c) optionally at least one assay component selected from a substrate for immobilization, a substrate for an enzymatic label, a reagent for conducting an RNA-based assay or an RT-qPCR assay, and computer software.

* * * * *